(12) United States Patent
Kikuchi

(10) Patent No.: US 12,272,051 B2
(45) Date of Patent: Apr. 8, 2025

(54) MEDICAL IMAGE PROCESSING APPARATUS, METHOD OF DRIVING MEDICAL IMAGE PROCESSING APPARATUS, MEDICAL IMAGING SYSTEM, AND MEDICAL SIGNAL ACQUISITION SYSTEM

(71) Applicant: Sony Group Corporation, Tokyo (JP)

(72) Inventor: Daisuke Kikuchi, Tokyo (JP)

(73) Assignee: Sony Group Corporation, Tokyo (JP)

( * ) Notice: Subject to any disclaimer, the term of this patent is extended or adjusted under 35 U.S.C. 154(b) by 678 days.

(21) Appl. No.: 17/604,998

(22) PCT Filed: May 26, 2020

(86) PCT No.: PCT/JP2020/020792
§ 371 (c)(1),
(2) Date: May 2, 2022

(87) PCT Pub. No.: WO2020/241651
PCT Pub. Date: Dec. 3, 2020

(65) Prior Publication Data
US 2022/0270243 A1  Aug. 25, 2022

(30) Foreign Application Priority Data
May 28, 2019  (JP) ................................. 2019-099715

(51) Int. Cl.
*G06T 7/00* (2017.01)
*G06V 10/24* (2022.01)
(Continued)

(52) U.S. Cl.
CPC ............ *G06T 7/0012* (2013.01); *G06V 10/24* (2022.01); *G06V 10/25* (2022.01); *G06V 10/62* (2022.01);
(Continued)

(58) Field of Classification Search
CPC ......... G06T 7/0012; G06T 2207/10064; G06T 2207/10068; G06V 10/24; G06V 10/25;
(Continued)

(56) References Cited

U.S. PATENT DOCUMENTS 9,222,870 B2  12/2015  Di Carlo
2008/0039695 A1*  2/2008  Takaoka ............... A61B 1/0655
600/178

(Continued)

FOREIGN PATENT DOCUMENTS

EP  2213222 A  8/2010
JP  2010-172530 A  8/2010
(Continued)

OTHER PUBLICATIONS

International Search Report and Written Opinion mailed on Jul. 7, 2020, received for PCT Application PCT/JP2020/020792, Filed on May 26, 2020, 9 pages including English Translation.
(Continued)

*Primary Examiner* — Santiago Garcia
(74) *Attorney, Agent, or Firm* — XSENSUS LLP

(57) ABSTRACT

A medical image processing apparatus includes an image processing unit configured to acquire a first fluorescence image captured between a timing when a first drug is administered and a first timing when a second drug is administered and a fluorescence intensity of a predetermined region starts to increase, and a second fluorescence image captured after the first timing and generate an output image in which fluorescence generated by the second drug is enhanced on a basis of the first fluorescence image and the second fluorescence image.

20 Claims, 12 Drawing Sheets

(51) Int. Cl.
*G06V 10/25* (2022.01)
*G06V 10/62* (2022.01)

(52) U.S. Cl.
CPC .............. *G06T 2207/10064* (2013.01); *G06T 2207/10068* (2013.01)

(58) Field of Classification Search
CPC .... G06V 10/62; A61B 1/00009; A61B 1/043; A61B 18/1482; A61B 1/045
See application file for complete search history.

(56) References Cited

U.S. PATENT DOCUMENTS

| | | | |
|---|---|---|---|
| 2012/0148140 A1* | 6/2012 | Di Carlo | G01N 1/31 382/133 |
| 2012/0271128 A1* | 10/2012 | Kubo | A61B 1/0661 600/317 |
| 2013/0012815 A1* | 1/2013 | Kubo | A61B 5/073 600/431 |
| 2013/0012864 A1* | 1/2013 | Kubo | A61B 1/041 604/20 |
| 2013/0216482 A1* | 8/2013 | Kwon | A61B 5/0071 424/9.6 |
| 2014/0324138 A1* | 10/2014 | Wentz | A61N 5/0622 607/90 |
| 2017/0020377 A1* | 1/2017 | Takeuchi | A61B 1/043 |
| 2019/0111156 A1* | 4/2019 | Lee | A61K 47/50 |
| 2019/0167083 A1* | 6/2019 | Watanabe | A61B 1/00 |
| 2019/0167086 A1* | 6/2019 | Kubo | A61B 1/043 |
| 2019/0224370 A1* | 7/2019 | Kolesky | A01N 1/0278 |
| 2020/0355694 A1* | 11/2020 | Aimiya | G01N 21/6458 |

FOREIGN PATENT DOCUMENTS

| | | |
|---|---|---|
| JP | 2019-48111 A | 3/2019 |
| WO | 2017/119340 A1 | 7/2017 |

OTHER PUBLICATIONS

Kusano, "All about ICG Fluorescence Navigation Surgery", Inter Medica Co., Ltd., 2008, p. 265.

* cited by examiner

FIG.6
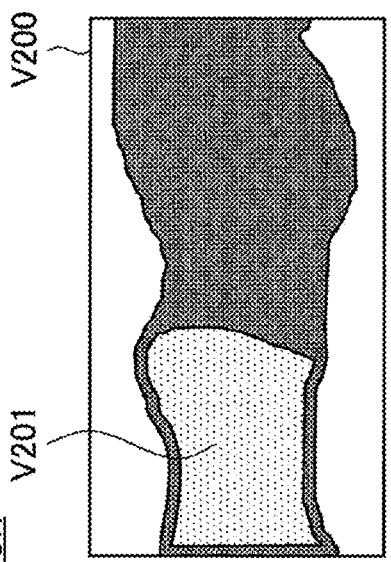
BEFORE ANASTOMOSIS
(AT TIME OF FIRST ADMINISTRATION
OF FLUORESCENT AGENT)
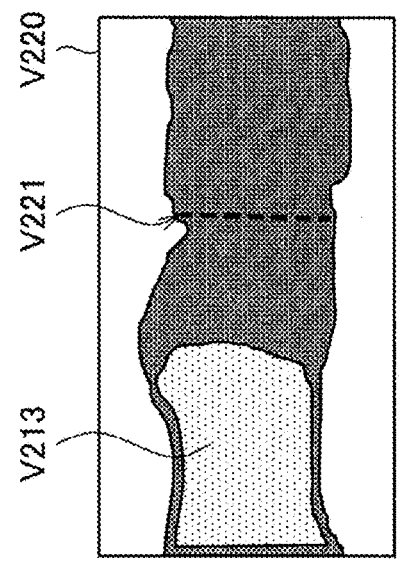
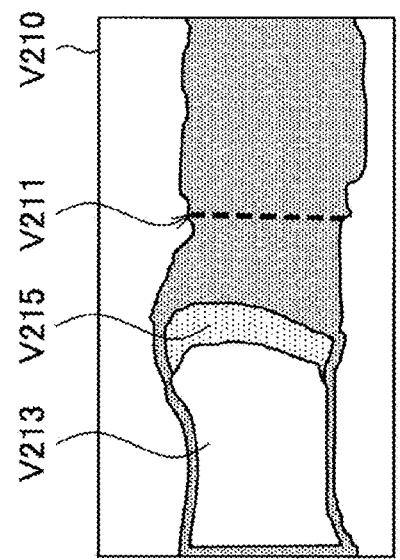
AFTER ANASTOMOSIS
(AT TIME OF SECOND ADMINISTRATION
OF FLUORESCENT AGENT)
NORMAL OBSERVATION
DISPLAY DIFFERENCE

MEDICAL IMAGE PROCESSING APPARATUS, METHOD OF DRIVING MEDICAL IMAGE PROCESSING APPARATUS, MEDICAL IMAGING SYSTEM, AND MEDICAL SIGNAL ACQUISITION SYSTEM

CROSS-REFERENCE TO RELATED APPLICATIONS

The present application is based on PCT filing PCT/JP2020/020792, filed May 26, 2020, which claims priority to JP 2019-099715, filed May 28, 2019, the entire contents of each are incorporated herein by reference.

FIELD

The present disclosure relates to a medical image processing apparatus, a method of driving the medical image processing apparatus, a medical imaging system, and a medical signal acquisition system.

BACKGROUND

With the development of surgical techniques, surgical instruments, and the like, surgery (so-called microsurgery) in which various types of treatments are performed while an affected part is observed with a medical observation device such as an endoscope, a surgical microscope, or the like has been frequently performed. In addition, among such medical observation devices, not only a device that can optically observe an affected part but also a device and a system that display an image of the affected part captured by an imaging device (a camera) or the like on a display device such as a monitor as an electronic image have been proposed.

Furthermore, in recent years, as an observation method using an observation device such as an endoscope or a surgical microscope, not only a method of observing an operative field by light in a visible light band but also various types of observation methods called special light observation have been proposed. Examples of the special light observation include narrow band imaging (NBI), fluorescence imaging (FI), infra-red imaging (IRI), and the like.

As a specific example, in the fluorescence imaging, a fluorescent material (in other words, a phosphor) with an affinity for a lesion such as a cancer is administered to a test subject (a patient) in advance, excitation light for exciting the fluorescent material is irradiated, and the lesion is observed using a fluorescence image (that is, an observation image based on a detection result of fluorescence) of fluorescence emitted from the fluorescent material accumulated in the lesion. For example, Patent Literature 1 discloses an outline of fluorescence imaging using indocyanine green (ICG) as a fluorescent material and an example of surgery based on the fluorescence imaging.

CITATION LIST

Non Patent Literature

Non Patent Literature 1: Mitsuo Kusano, "All about ICG Fluorescence Navigation Surgery", INTER MEDICA Co., Ltd., 2008, p.265

SUMMARY

Technical Problem

Meanwhile, when a drug containing a fluorescent material (hereinafter, also referred to as "fluorescent agent") is administered and fluorescence imaging is performed, the fluorescent material (for example, ICG) adheres to a blood vessel wall, a protein in a tissue, or the like through a blood flow, and in some cases, fluorescence is emitted for a while. Due to such properties, under a situation in which a fluorescent agent is administered a plurality of times, at the time of the second and subsequent administrations of the fluorescent agent, a fluorescent material as a result of the previous administration and a fluorescent material as a result of the new administration are mixed, and visibility may decrease. In order to handle such a situation, as an example of a method of ensuring visibility, there is a method of performing observation after the fluorescent material remaining in an observation region is released (washed out). However, in a case where this method is applied, it takes time before the fluorescent material is released, and as a result, the time required for observation tends to be longer.

Therefore, the present disclosure proposes a technology that enables an image acquired in response to a drug to be observed in a more suitable manner even in a situation in which the drug is administered a plurality of times.

Solution to Problem

According to the present disclosure, a medical image processing apparatus comprises an image processing unit configured to acquire a first fluorescence image captured between a timing when a first drug is administered and a first timing when a second drug is administered and a fluorescence intensity of a predetermined region starts to increase, and a second fluorescence image captured after the first timing and generate an output image in which fluorescence generated by the second drug is enhanced on a basis of the first fluorescence image and the second fluorescence image.

Furthermore, according to the present disclosure, a method of driving a medical image processing apparatus comprises causing a computer to acquire a first fluorescence image captured between a timing when a first drug is administered and a first timing when a second drug is administered and a fluorescence intensity of a predetermined region starts to increase, and a second fluorescence image captured after the first timing, and generate an output image in which fluorescence generated by the second drug is enhanced on a basis of the first fluorescence image and the second fluorescence image.

Moreover, according to the present disclosure, a medical imaging system comprises: a light source configured to emit excitation light of a fluorescent material contained in a drug to be administered to a patient; an imaging unit configured to receive and capture an image of light including fluorescence generated by the drug; and an image processing apparatus configured to generate an output image in which fluorescence generated by a second drug is enhanced on a basis of a first fluorescence image captured between a timing when a first drug is administered and a first timing when the second drug is administered and a fluorescence intensity of a predetermined region starts to increase, and a second fluorescence image captured after the first timing.

Moreover, according to the present disclosure, a medical image processes apparatus comprising an image processing unit configured to output an output image that corresponds to an imaging result of an affected part of a patient by an imaging unit and in which light belonging to a wavelength band corresponding to a drug to be administered to the patient is set as an imaging target, wherein the image processing unit includes, as an operation mode, a first mode for outputting an output image corresponding to an imaging result of the affected part at that time, and a second mode for outputting an output image in which fluorescence generated by a second drug is enhanced on a basis of a first fluorescence image captured between a timing when a first drug is administered and a first timing when the second drug is administered and a fluorescence intensity of a predetermined region starts to increase, and a second fluorescence image captured after the first timing.

Moreover, according to the present disclosure, a medical signal acquisition system comprises: a light source configured to emit light in a wavelength band corresponding to a drug to be administered to a patient; an acquisition unit configured to acquire an optical signal belonging to a wavelength band corresponding to the drug; and an optical signal extraction unit configured to extract an optical signal generated by a second drug on a basis of a first optical signal acquired between a timing when a first drug is administered and a first timing when the second drug is administered and a fluorescence intensity of a predetermined region starts to increase, and a second optical signal acquired after the first timing.

BRIEF DESCRIPTION OF DRAWINGS

FIG. 6 is an explanatory diagram for explaining an example of the medical observation system according to the embodiment.

DESCRIPTION OF EMBODIMENTS

Figure 1:
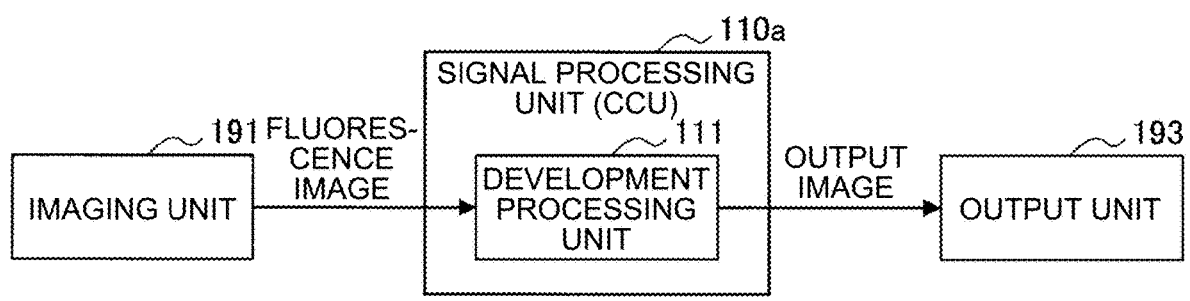
FIG. 1 is a functional block diagram illustrating an example of a functional configuration of a medical observation system according to one embodiment of the present disclosure.

Hereinafter, preferred embodiments of the present disclosure will be described in detail with reference to the accompanying drawings. Note that, in the present specification and the drawings, components having substantially the same functional configuration are denoted by the same reference numerals, and redundant description is omitted.

Note that the description will be given in the following order.
1. Introduction
2. Technical Feature
    2.1. Functional Configuration
    2.2. Signal Processing
    2.3. Flow of Processing
    2.4. Example
    2.5. Modification
3. Example of Hardware Configuration
4. Application Example
    4.1. First Application Example: Microscope Imaging System
    4.2. Second Application Example: Endoscopic Surgical System
5. Conclusion

1. INTRODUCTION

First, as an example of an observation method using a drug, among observation methods referred to as so-called special light observation, in particular, an outline of fluorescence imaging for observing a fluorescence image of a lesion part by using a fluorescent material will be described, and then technical problems of a medical observation system according to the present disclosure will be described.

In the fluorescence imaging, a fluorescent material with an affinity for a lesion such as a cancer is administered to a test subject (a patient) in advance, excitation light for exciting the fluorescent material is irradiated, and the lesion is observed using a fluorescence image (that is, an observation image based on a detection result of fluorescence) of fluorescence emitted from the fluorescent material accumulated in the lesion part.

A typical example of the fluorescent material used for fluorescence imaging is indocyanine green (ICG). ICG emits fluorescence (that is, light in a near-infrared band) with a wavelength of around 820 nm by using light with a wavelength of around 808 nm as excitation light.

Furthermore, in recent years, various types of fluorescent materials other than ICG have been proposed as fluorescent materials used for fluorescence imaging from the viewpoints of, for example, the property of more selectively accumulating in a lesion such as a cancer, the reduction of the influence (the side effect) on a test subject as a result of administration, and the like. In addition, among such fluorescent materials, a fluorescent material that emits fluorescence in a wavelength band different from that of ICG and a fluorescent material that emits light belonging to a visible-light wavelength band have also been proposed.

In the fluorescence imaging, for example, by observing the presence or absence of fluorescence emitted from the fluorescent material such as ICG and the temporal change of the fluorescence, the operator can visually observe a blood flow and a lymph flow. In addition, by analyzing the temporal change (that is, the temporal change of the fluorescent material flowing in the body of a patient) of the fluorescence emitted from the fluorescent material, for example, it is also possible to discriminate between a portion with a good flow and a portion with a poor flow in a part where a desired medium (for example, blood or lymph) flows, such as a blood vessel or a lymph vessel.

Meanwhile, as a problem in a case where the fluorescence imaging using the fluorescent material such as ICG is used for surgery, when fluorescence contrast imaging is performed by administering a fluorescent agent, the fluorescent material adheres to a blood vessel wall, a protein in a tissue, or the like through a blood flow, and in some cases, fluorescence is emitted for a while. Under such a situation, in a case where the administration of the fluorescent agent and the fluorescence imaging are repeatedly performed in a relatively short period of time, at the time of the administration of the fluorescent agent, a fluorescent material as a result of the previous administration and a fluorescent material as a result of the new administration may be mixed. In such a case, since the fluorescence emitted by the fluorescent material as a result of the previous administration remains, in some cases, the visibility of the fluorescence emitted by the fluorescent material as a result of the new administration decreases. In order to handle such a situation, as an example of a method of ensuring visibility, there is a method of performing observation after the fluorescent material remaining in an observation region is released (washed out). However, in a case where this method is applied, it takes time before the fluorescent material is released, and as a result, the time required for observation tends to be longer.

In view of the above circumstances, the present disclosure proposes a technology that enables an image acquired in response to a drug to be observed in a more suitable manner even in a situation in which the drug is administered a plurality of times.

Specifically, a technology is proposed that enables a fluorescence image corresponding to the imaging result of fluorescence emitted by a fluorescent material as a result of the administration of a new fluorescent agent to be observed in a more suitable manner before the release of the fluorescent material even under a situation in which the administration of the fluorescent agent and fluorescence imaging are repeatedly performed.

2. TECHNICAL FEATURE

Next, the technical features of the medical observation system according to one embodiment of the present disclosure will be described. Note that, hereinafter, the technical features of the medical observation stem according to the present embodiment will be described by particularly focusing on a case where a fluorescent agent containing a predetermined fluorescent material is administered to a patient and an affected part is observed on the basis of a fluorescence image corresponding to the imaging result of fluorescence emitted by the fluorescent material.

<2.1. Functional Configuration>

First, an example of a functional configuration of the medical observation system according to the present embodiment will be described. The medical observation system according to the present embodiment is configured to be operable by selectively switching between a normal observation mode and a difference display mode. The normal observation mode is a mode for outputting a fluorescence image corresponding to the imaging result of an affected part at that time by an imaging unit (for example, an endoscope device, a microscope device, or the like). In addition, the difference display mode is a mode in which under a situation in which the administration of a fluorescent agent and fluorescence imaging are repeatedly performed, the influence of fluorescence emitted by a fluorescent material previously administered is reduced, so that the fluorescence image corresponding to the imaging result of fluorescence emitted by a fluorescent material newly administered can be observed in a more suitable manner. Consequently, in this section, an example of a functional configuration of the medical observation system according to the present embodiment will be described separately for the operation in the normal observation mode and for the operation in the difference display mode. Note that the normal observation mode corresponds to an example of "first mode", and the difference display mode corresponds to an example of "second mode".

First, an example of the functional configuration of the medical observation system according to the present embodiment in a case where the medical observation system operates in the normal observation mode will be described with reference to FIG. 1. FIG. 1 is a functional block diagram illustrating an example of a functional configuration of a medical observation system 11 according to the present embodiment, and illustrates an example of the functional configuration in a case where the medical observation system 11 operates in the normal observation mode. Note that, hereinafter, in a case where the medical observation system 11 at the time of the operation in the normal observation mode is particularly described, it is also referred to as "medical observation system 11a" for convenience. On the other hand, in a case where the medical observation system 11 at the time of the operation in the difference display mode is particularly described, it is also referred to as "medical observation system 11b" for convenience.

As illustrated in FIG. 1, the medical observation system 11a includes an imaging unit 191, a signal processing unit 110, and an output unit 193. Note that, in the following description, in a case where the signal processing unit 110 at the time of the operation in the normal observation mode is particularly described, it is also referred to as "signal processing unit 110a" for convenience as illustrated in FIG. 1. On the other hand, in a case where the signal processing unit 110 at the time of the operation in the difference display mode is particularly described, it is also referred to as "signal processing unit 110b" for convenience.

It is schematically illustrated that the imaging unit 191 receives light from an affected part (an observation target) to capture an image of the affected part. As a specific example, the imaging unit 191 can be configured as a part (for example, a camera head) of an endoscope device or a surgical microscope device. The imaging unit 191 outputs an image corresponding to the imaging result of the affected part to the signal processing unit 110a. Note that, under a situation in which fluorescence imaging is performed, an image signal (in other words, a fluorescence image) corresponding to the imaging result of fluorescence emitted by a fluorescent material contained in a fluorescent agent administered to the patient is output from the imaging unit 191 to the signal processing unit 110a.

The output unit 193 presents various types of information to a user. In the medical observation system 11 according to the present embodiment, the output unit 193 is configured as a display unit such as a so-called display, and presents information to the user by displaying display information such as an image (a still image or a moving image). As a specific example, the output unit 193 may display an output image (a fluorescence image) output from the signal processing unit 110a to be described later.

The signal processing unit 110 is configured as a so-called camera control unit (CCU), generates an output image by performing various types of image processing on an image signal (for example, a fluorescence image) output from the imaging unit 191, and causes the output unit 193 to output the output image. As illustrated in FIG. 1, the signal processing unit 110a includes a development processing unit 111.

The development processing unit 111 performs predetermined image processing (so-called development processing) on an image signal output from the imaging unit 191 every predetermined unit period (for example, every frame) to generate an output image. In the example illustrated in FIG. 1, the development processing unit 111 sequentially outputs the output image generated to the output unit 193. As a result, the output image is presented to the user (for example, a doctor) via the output unit 193.

An example of the functional configuration of the medical observation system according to the present embodiment in a case where the medical observation system operates in the normal observation mode has been described with reference to FIG. 1.

Figure 2:
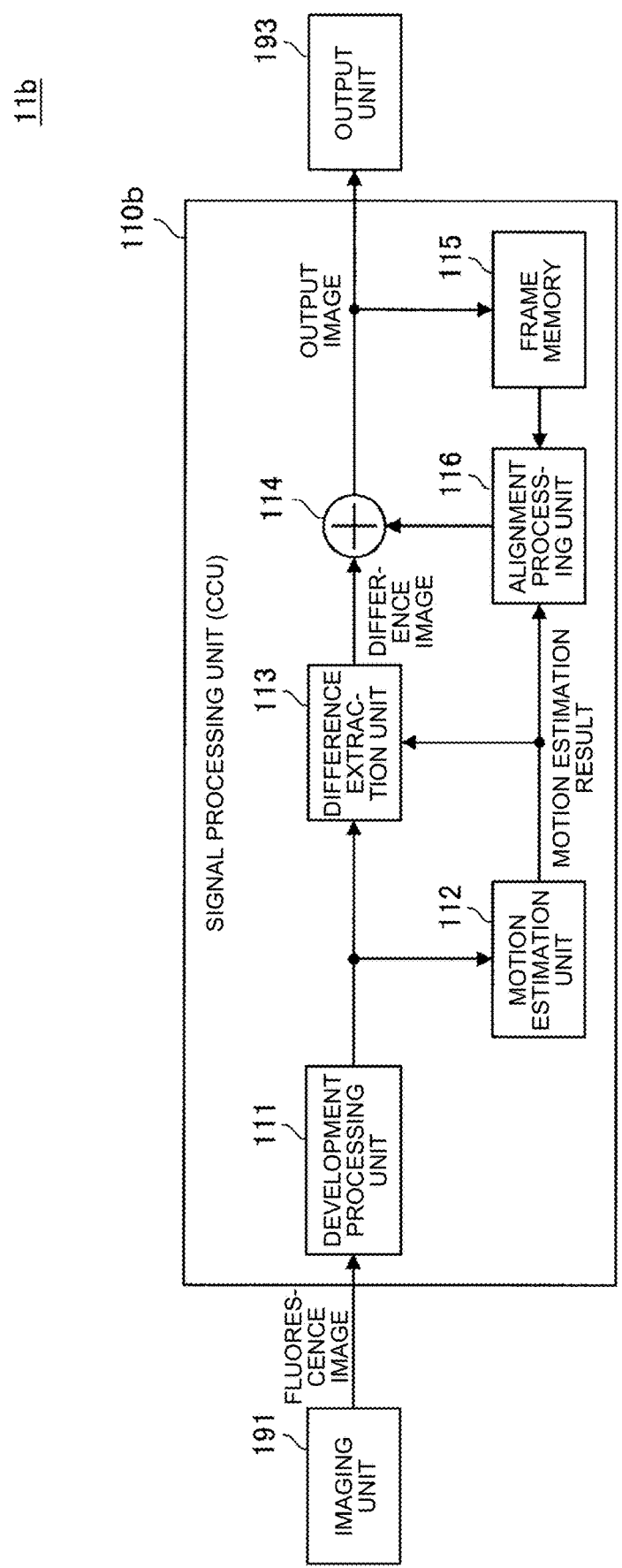
FIG. 2 is a functional block diagram illustrating an example of the functional configuration of the medical observation system according to the embodiment.

Next, an example of the functional configuration of the medical observation system according to the present embodiment in a case where the medical observation system operates in the difference display mode will be described with reference to FIG. 2. FIG. 2 is a functional block diagram illustrating an example of the functional configuration of the medical observation system according to the present embodiment, and illustrates an example of the functional configuration in a case where the medical observation system operates in the difference display mode.

As illustrated in FIG. 2, the medical observation system 11b includes the imaging unit 191, the signal processing unit 110b, and the output unit 193. Note that the imaging unit 191 and the output unit 193 are similar to the example illustrated in FIG. 1, and thus detailed description thereof is omitted. Furthermore, the signal processing unit 110 corresponds to an example of "image processing unit". Moreover, a device including the signal processing unit 110 corresponds to an example of "medical image processing apparatus".

As illustrated in FIG. 2, the signal processing unit 110b includes the development processing unit 111, a motion estimation unit 112, a difference extraction unit 113, an addition unit 114, a frame memory 115, and an alignment processing unit 116. Note that the development processing unit 111 is substantially similar to the example illustrated in FIG. 1, and thus detailed description thereof is omitted.

The motion estimation unit 112 compares a plurality of images (for example, images corresponding to imaging results in different frames) corresponding to imaging results at different timings, the images being output from the development processing unit 111, to estimate a relative motion (in other words, a motion of an affected part in the image) between the imaging unit 191 and a subject (for example, an affected part to be observed). As a specific example, the motion estimation unit 112 calculates a motion vector (that is, the direction and the amount of change of a motion) between timings (for example, between frames) corresponding to the plurality of images every predetermined unit data (for example, on a pixel basis). Examples of a motion estimation method include a block matching method and a gradient method. Furthermore, the motion estimation unit 112 may improve the accuracy of motion estimation by estimating the motion of the affected part in the image between the images on the basis of each of a plurality of motion estimation methods and combining the respective estimation results. The motion estimation unit 112 then outputs the estimation result of the motion of the affected part in the image to the difference extraction unit 113 and the alignment processing unit 116.

On the basis of the estimation result of the motion of the affected part in the image output from the motion estimation unit 112, the difference extraction unit 113 calculates (extracts) a difference between the plurality of images corresponding to the imaging results at different timings, the images being output from the development processing unit 111, to generate a difference image. Note that, in the following description, for convenience, it is assumed that the difference image is generated for an image (hereinafter, also referred to as "current frame image") corresponding to the imaging result in the current frame and an image (hereinafter, also referred to as "previous frame image") captured in a frame before the current frame.

As a specific example, the difference extraction unit 113 shifts (that is, corrects) the previous frame image on a pixel basis on the basis of the estimation result of the motion of the affected part in the image to perform an alignment between the current frame image and the previous frame image. The difference extraction unit 113 then calculates (extracts) a difference (for example, an inter-frame difference) between the current frame image and the previous frame image after the alignment, and generates a difference image corresponding to the calculation result of the difference.

As described above, the difference extraction unit 113 generates a difference image on the basis of images (for example, fluorescence images) sequentially output from the development processing unit 111, and outputs the difference image to the addition unit 114.

The frame memory 115 temporarily holds an output image output from the addition unit 114 to be described later. The output image held in the frame memory 115 is read at a desired timing by the alignment processing unit 116 to be described later.

In addition, on the basis of a predetermined trigger, the frame memory 115 excludes the output image held until the trigger is received from the output target to the alignment processing unit 116. As a specific example, by discarding the output image held until the trigger is received on the basis of a predetermined trigger, the output image may be excluded from the output target to the alignment processing unit 116. In addition, the frame memory 115 may separately hold the output image held until the trigger is received, thereby excluding the output image from the output target to the alignment processing unit 116. As a result, both the past output image separately held and the output image newly held in the frame memory 115 can also be set as output targets.

Note that the timing when the trigger is generated and the type of the trigger are not particularly limited. For example, by using a change in the operation mode of the medical observation system 11 as a trigger, the output image held by the frame memory 115 may be excluded from the output target to the alignment processing unit 116. As a more specific example, by using the transition to the difference display mode as a trigger, the frame memory 115 may exclude the output image held until the trigger is received from the output target to the alignment processing unit 116. Note that the frame memory 115 corresponds to an example of "storage unit".

The alignment processing unit 116 reads the output image (that is, the past output image) held in the frame memory 115, and shifts (that is, corrects) the output image on the basis of the estimation result of the motion of the affected part in the image output from the motion estimation unit 112. The alignment processing unit 116 then outputs the shifted output image to the addition unit 114. As a result, the alignment is performed between the difference image output from the difference extraction unit 113 to the addition unit 114 and the past output image output from the alignment processing unit 116 to the addition unit 114.

The addition unit 114 adds the difference image output from the difference extraction unit 113 to the past output image output from the alignment processing unit 116 to newly generate an output image (that is, an output image corresponding to the current frame). The addition unit 114 then causes the output unit 193 to output the output image generated. Furthermore, the addition unit 114 causes the frame memory 115 to hold the output image. That is, as described above, the output image held in the frame memory 115 is added to the difference image generated thereafter as the past output image, and thus a new output image is generated. As described above, in the example illustrated in FIG. 2, the difference image is accumulated in the frame memory 115, and the output image corresponding to the accumulation result is output via the output unit 193. Note that the difference image output from the difference extraction unit 113 corresponds to an example of "first difference image", and the difference image accumulated in the frame memory 115 corresponds to an example of "second difference image".

An example of the functional configuration of the medical observation system according to the present embodiment in a case where the medical observation system operates in the difference display mode has been described above with reference to FIG. 2.

Note that the above is only an example, and the functional configuration of the medical observation system 11 is not necessarily limited to the example illustrated in FIGS. 1 and 2 as long as each function described above can be implemented. As a specific example, two or more configurations among the respective configurations of the medical observation system 11 may be integrally configured. Furthermore, as another example, some of the configurations of the signal processing unit 110 may be provided outside the signal processing unit 110. Further, the configuration related to the generation of an image based on an image signal in the signal processing unit 110, such as the development processing unit 111, may be provided outside the signal processing unit 110.

Furthermore, although not illustrated in FIGS. 1 and 2, the medical observation system 11 may include a light source that emits light belonging to a wavelength band corresponding to a drug to be administered to a patient. As a specific example, the light source may be configured to be capable of emitting excitation light of a fluorescent material contained in a fluorescent agent to be administered to the patient. With such a configuration, it is possible to excite the fluorescent material contained in the fluorescent agent with the light emitted from the light source, thereby causing the fluorescent material to emit fluorescence.

In addition, the medical observation system 11 may be configured to be capable of outputting both a fluorescence image that is output at the time of the operation in the normal observation mode and a fluorescence image that is output at the time of the operation in the difference observation mode. In this case, for example, in the medical observation system 11 illustrated in FIG. 2, it suffices that the image output from the development processing unit 111 is separately output to the output unit 193 as an output image.

<2.2. Signal Processing>

Figure 3:
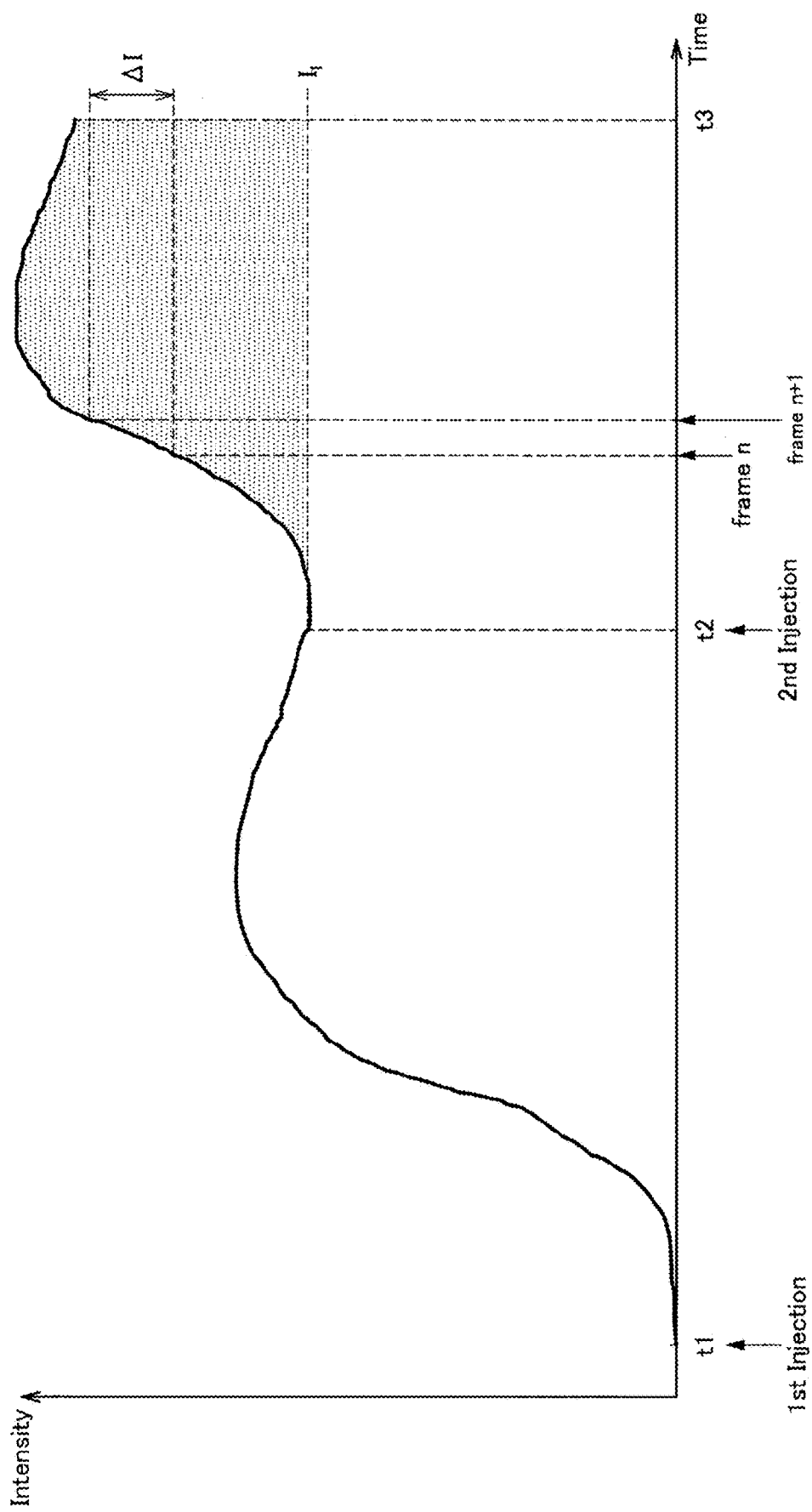
FIG. 3 is an explanatory diagram for explaining an outline of an example of signal processing on an image signal in the medical observation system according to the embodiment.
Figure 4:
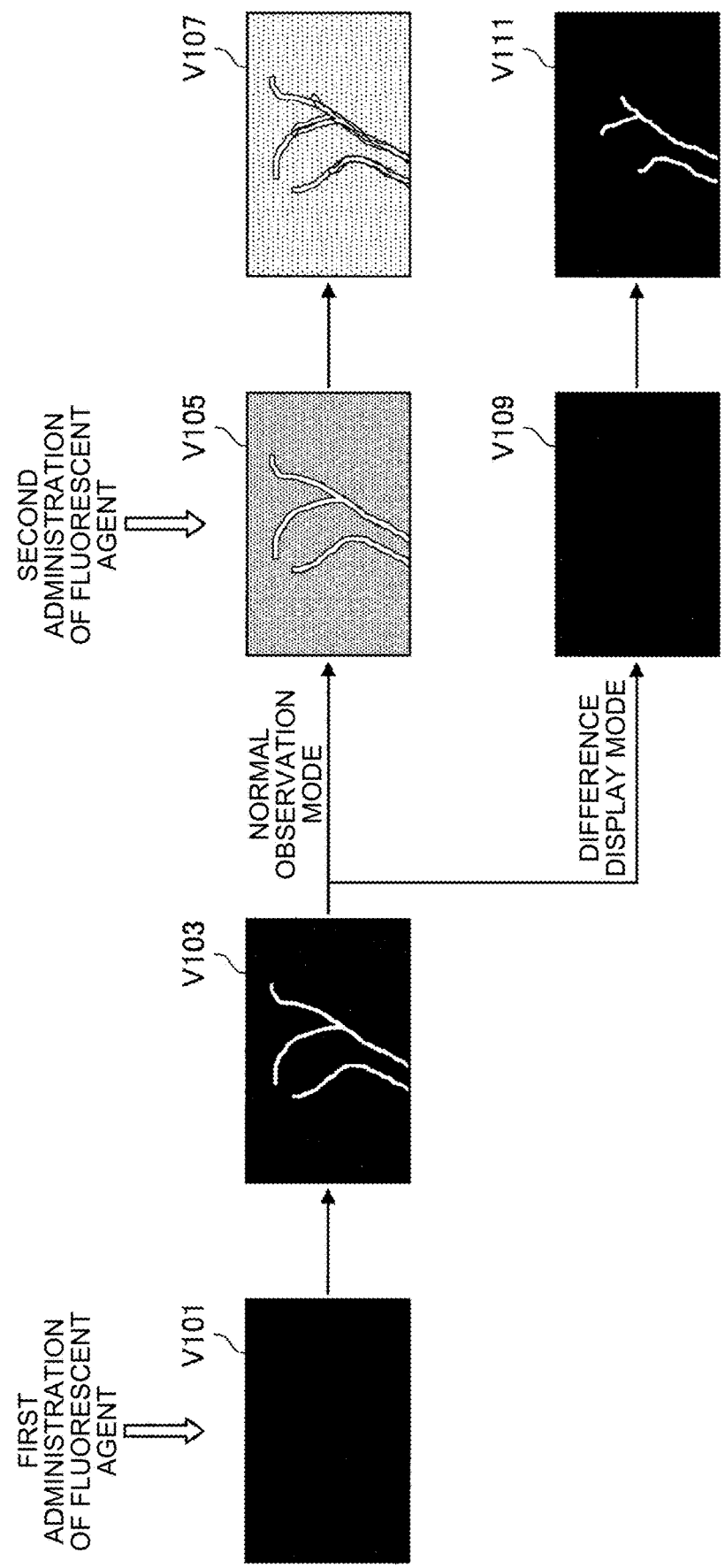
FIG. 4 is an explanatory diagram for explaining the outline of an example of the signal processing on the image signal in the medical observation system according to the embodiment.

Next, an example of signal processing (that is, image processing) on an image signal in the medical observation system according to the present embodiment will be described in more detail with reference to FIGS. 3 and 4. FIGS. 3 and 4 are explanatory diagrams for explaining an outline of an example of the signal processing on the image signal in the medical observation system according to the present embodiment.

For example, FIG. 3 schematically illustrates a time-series change in the luminance (that is, a change in the fluorescence intensity) of a predetermined part (for example, a predetermined pixel) of an image in a case where a fluorescent agent is administered a plurality of times at different timings under a situation in which fluorescence imaging is performed. In the example illustrated in FIG. 3, the horizontal axis represents the time, and the vertical axis represents the luminance value (that is, the fluorescence intensity). That is, the graph of FIG. 3 illustrates a time-series change in the fluorescence intensity of a predetermined area (hereinafter, also referred to as "pixel of interest" for convenience) in the image. Furthermore, in FIG. 3, a timing t1 indicates a timing corresponding to the detection result of a first administration of the fluorescent agent, and ideally corresponds to the timing when the fluorescent agent is administered for the first time. Further, a timing t2 indicates a timing corresponding to the detection result of a second administration of the fluorescent agent, and ideally corresponds to the timing when the fluorescent agent is administered for the second time. Moreover, a timing t3 indicates the output timing of a fluorescence image corresponding to the second administration result of the fluorescent agent.

As illustrated in FIG. 3, when the fluorescent agent is administered for the first time at the timing t1, the fluorescent material flows into the region (for example, the site of interest) corresponding to the pixel of interest with the diffusion of the fluorescent material, so that a fluorescence intensity I of the pixel of interest increases in time series. Furthermore, with the start of emission (washout) of the fluorescent material from the region (the site of interest) corresponding to the pixel of interest, the fluorescence intensity I of the pixel of interest decreases in time series. Next, when the administration of the fluorescent agent is performed for the second time at the timing t2, as the fluorescent material newly administered diffuses, the fluorescence intensity I of the pixel of interest increases again in time series. Note that, in FIG. 3, a reference numeral $I_1$ indicates the fluorescence intensity of the pixel of interest at the timing t2. That is, the component exceeding the fluorescence intensity $I_1$ after the timing t2 corresponds to a change in the fluorescence intensity caused by the detection result of the fluorescence emitted by the fluorescent material contained in the fluorescent agent administered for the second time.

Meanwhile, as in the example illustrated in FIG. 3, after the timing t2 when the second administration of the fluorescent agent is performed, the detection result of the fluorescence emitted by the fluorescent material contained in the fluorescent agent administered for the first time is apparent. That is, at the time of the operation in the normal observation mode, after the timing t2, the fluorescence intensity corresponding to the detection result of the fluorescence emitted by the newly administered fluorescent material is further added with the fluorescence intensity $I_1$ as a reference point. That is, the entire screen may become brighter due to the influence of the detection result of the fluorescence emitted by the fluorescent material administered for the first time, and as a result, the visibility may decrease.

On the other hand, as described above, at the time of the operation in the difference display mode, for example, the output image held in the frame memory 115 is discarded on the basis of a predetermined trigger (that is, the frame memory 115 is reset). For example, in the case of the example illustrated in FIG. 3, it is assumed that the frame memory 115 is reset at the timing t2 on the basis of the detection result of the second administration of the fluorescent agent. In this case, the output image is generated on the basis of the component exceeding the fluorescence intensity I₁ after the timing t2.

Specifically, in a case where the change in fluorescence intensity between frames is indicated by ΔI, the change in fluorescence intensity from the timing t2 to the timing t3 is expressed by a formula shown as (Formula 1) below.

$$I = \sum_{t2}^{t3} \Delta I \quad (1)$$

As described above, at the time of the operation in the difference display mode, the image that is output after the second administration of the fluorescent agent is generated on the basis of (Formula 1) described above.

That is, in this case, the output image is generated on the basis of the component exceeding the fluorescence intensity I₁ after the timing t2.

Here, an example of an output image presented in each of the normal observation mode and the difference display mode will be described with reference to FIG. 4. In FIG. 4, a reference numeral V101 schematically indicates an output image (a fluorescence image) immediately after the first administration of a fluorescent agent, that is, an output image at the timing t1 illustrated in FIG. 3. In addition, a reference numeral V103 schematically indicates an output image (a fluorescence image) immediately before the second administration of the fluorescent agent, that is, an output image immediately before the timing t2 illustrated in FIG. 3.

In addition, a reference numeral V105 schematically indicates an output image (a fluorescence image) immediately after the second administration of the fluorescent agent, that is, an output image immediately after the timing t2 illustrated in FIG. 3, at the time of the operation in the normal observation mode. Moreover, a reference numeral V107 schematically indicates an output image (a fluorescence image) that is output after the second administration of the fluorescent agent, that is, an output image that is output at the timing t3 illustrated in FIG. 3, at the time of the operation in the normal observation mode.

At the time of the operation in the normal observation mode, when the second administration of the fluorescent agent is performed, the detection result (the fluorescence intensity) of fluorescence emitted by a fluorescent material contained in the newly administered fluorescent agent is added on the output image V103 immediately before the administration. That is, in the output images V105 and V107 that are output thereafter, since the detection result of the fluorescence corresponding to the first administration of the fluorescent agent remains, the entire image is brighter than the output image V103, and is a whitish image as a whole as illustrated in FIG. 4, for example. As a result, at the time of the operation in the normal observation mode, for example, a decrease in contrast, blown out highlights, or the like may occur in the output image presented after the second administration of the fluorescent agent, and the visibility may decrease.

On the other hand, a reference numeral V109 schematically indicates an output image (a fluorescence image) immediately after the second administration of the fluorescent agent, that is, an output image immediately after the timing t2 illustrated in FIG. 3, at the time of the operation in the difference display mode. Moreover, a reference numeral V111 schematically indicates an output image (a fluorescence image) that is output after the second administration of the fluorescent agent, that is, an output image that is output at the timing t3 illustrated in FIG. 3, at the time of the operation in the difference display mode.

In the example illustrated in FIGS. 3 and 4, at the time of the operation in the difference display mode, the frame memory 115 is reset at the timing of the second administration of the fluorescent agent, as illustrated as the output image V109. For this reason, in this case, the detection result of fluorescence in the part where the fluorescence intensity has increased after the second administration of the fluorescent agent is reflected in the output image. As a result, as illustrated as the output image V111, it is possible to ensure visibility equivalent to that at the time of observation after the first administration of the fluorescent agent, even at the time of observation after the second administration of the fluorescent agent.

Note that, in the present disclosure, in a case where a drug is administered a plurality of times, a drug administered first corresponds to an example of "first drug", and a drug administered after the first drug corresponds to an example of "second drug". Specifically, in the example illustrated in FIGS. 3 and 4, the fluorescent agent administered at the timing t1 corresponds to an example of "first drug", and the fluorescent agent administered at the timing t2 corresponds to "second drug". Note that, in the example illustrated in FIG. 3, it is assumed that the first drug and the second drug are the same type of drug, but the first drug and the second drug may be different types of drugs. In addition, the fluorescence image captured between the timing when the first drug is administered and the timing when the second drug is administered corresponds to an example of "first fluorescence image", and a fluorescence image captured after the timing when the second drug is administered corresponds to an example of "second fluorescence image". Specifically, in the example illustrated in FIG. 4, the fluorescence image V103 corresponds to an example of "first fluorescence image", and the fluorescence image V111 corresponds to an example of "second fluorescence image". That is, according to the medical observation system of the present embodiment, it is possible to generate, as the output image, the fluorescence image V111 in which the fluorescence generated by the second drug (for example, the fluorescent agent administered for the second and subsequent times) is enhanced.

Note that, in the example illustrated in FIG. 3, the method of detecting the timing when the fluorescent agent is administered, which triggers the reset of the frame memory 115, is not particularly limited. As a specific example, in a case where a predetermined operation is performed by a user in accordance with the administration of the fluorescent agent, the signal processing unit 110 may detect the operation to detect the timing when the fluorescent agent is administered.

Furthermore, as another example, the signal processing unit 110 may perform image analysis on an image (a fluorescence image) corresponding to the imaging result of the imaging unit 191 to detect the timing when the fluorescent agent is administered. As a specific example, in the case of the example illustrated in FIG. 3, it is possible to detect the timing t1 of the first administration of the fluorescent agent by detecting the rise of the luminance value (the fluorescence intensity). In addition, by detecting the minimum value of the change in luminance value, that is, the timing when the luminance value decreasing in time series starts increasing again, it is possible to detect the timing of the second and subsequent administrations of the fluorescent agent (for example, the timing t2 of the second administration of the fluorescent agent). Note that the timing when the luminance value decreasing in time series starts increasing again corresponds to an example of "first timing".

It is needless to mention that the above is only an example, and the method is not particularly limited as long as the signal processing unit 110 can detect the timing of the administration of the fluorescent agent. In addition, although an example of a case where fluorescence imaging is performed has been described above, even in a case where an observation method other than fluorescence imaging is applied, the method is not particularly limited as long as it is possible to detect the timing when the drug to be used is administered, and the detection method may be selectively switched according to the observation method or the drug to be used. Furthermore, the above is only an example, and does not necessarily limit the function of the medical observation system according to the present embodiment. For example, in acquiring an image corresponding to the first fluorescence image or the second fluorescence image, it is not always necessary to explicitly detect the timing when the first drug or the second drug is administered. As a specific example, in the example illustrated in FIG. 3, by setting an image (a fluorescence image) corresponding to the imaging result of the transition of the fluorescence intensity in which the fluorescence intensity rises, falls, and rises again as the first fluorescence image, it is possible to generate the output image without explicitly detecting the timing of the administration of the drug.

Furthermore, the above example has described an example of a case where the same type of fluorescent agent is administered a plurality of times, but the application range of the medical observation system according to the present embodiment is not necessarily limited, and for example, a plurality of types of fluorescent agents may be administered individually for each observation. That is, as long as it is possible to detect each fluorescence emitted by the fluorescent material contained in each of the plurality of types of fluorescent agents, it is also possible to selectively use any fluorescent agent among the plurality of types of fluorescent agents for each of a plurality of observations.

Further, in the example illustrated in FIG. 4, the fluorescence image V103 held in the frame memory 115 may be separately held without being discarded at the timing of the second administration of the fluorescent agent. With such a configuration, it is also possible to output the fluorescence image V103 before the second administration of the fluorescent agent and the fluorescence image V111 after the second administration of the fluorescent agent in a comparable manner.

An example of the signal processing (that is, the image processing) on the image signal in the medical observation system according to the present embodiment has been described in more detail with reference to FIGS. 3 and 4.

<2.3. Flow of Processing>

Next, an example of a flow of a series of processing of the medical observation system according to the present embodiment will be described particularly focusing on the processing of the signal processing unit. For example, FIG. 5 is a flowchart illustrating an example of the flow of a series of processing of the medical observation system according to the present embodiment, and in particular, illustrates an example of an operation in a case where the administration of a fluorescent agent and fluorescence imaging are repeatedly performed.

Figure 5:
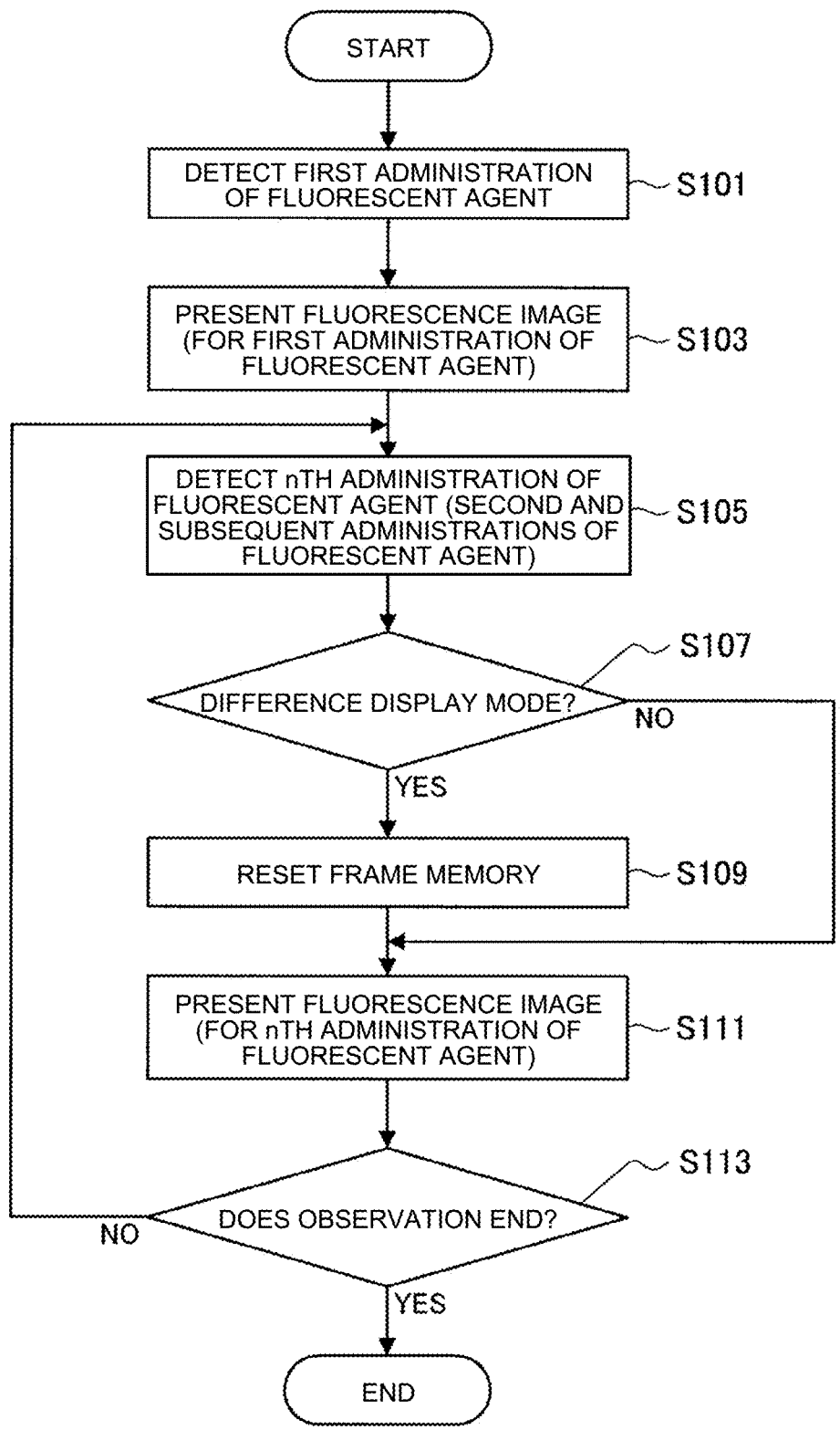
FIG. 5 is a flowchart illustrating an example of a flow of a series of processing of the medical observation system according to the embodiment.

As illustrated in FIG. 5, when the first administration of the fluorescent agent is detected (S101), the signal processing unit 110 generates an output image on the basis of a fluorescence image corresponding to the imaging result of the imaging unit 191, and causes the output unit 193 to output the output image (S103). As a result, the fluorescence image corresponding to the detection result of fluorescence emitted by a fluorescent material contained in the fluorescent agent administered for the first time is presented via the output unit 193.

Next, when the nth (second and subsequent) administration of the fluorescent agent is detected (S105), the signal processing unit 110 resets the frame memory 115 (S109) in a case where the operation mode is the difference display mode (S107, YES). In this case, the signal processing unit 110 presents an output image corresponding to the detection result of the fluorescence after the reset, that is, an output image corresponding to the detection result of the fluorescence emitted by the fluorescent material contained in the fluorescent agent administered for the nth time (S111). As a specific example, the output image V111 in the example illustrated in FIG. 4 corresponds to an example of the output image presented in this case.

On the other hand, when the operation mode is the normal mode (S107, NO), the signal processing unit 110 does not reset the frame memory 115 (S109). In this case, the signal processing unit 110 presents an output image reflecting the detection result of fluorescence as a result of a series of administrations of the fluorescent agent during the operation in the normal mode (S111). As a specific example, the output image V107 in the example illustrated in FIG. 4 corresponds to an example of the output image presented in this case.

Note that although not clearly illustrated in the example illustrated in FIG. 5, the operation mode may be appropriately switched at a desired timing, and the method of switching the operation mode is not particularly limited either. As a specific example, the signal processing unit 110 may switch the operation mode to the difference display mode in a case where the operation mode is the normal observation mode at the time of detection of the nth (the second and subsequent) administration of the fluorescent agent (S015). In addition, even when the operation mode is switched, the signal processing unit 110 may switch whether or not to reset the frame memory 115 (S109) according to the setting of the operation mode at the timing of performing the processing indicated by the reference numeral S107. As a result, the output image based on the setting of the operation mode at that time is presented.

The signal processing unit 110 repeatedly performs a series of processing indicated by the reference numerals S105 to S111 unless the end of observation is instructed (S113, NO). Then, when the end of the observation is instructed (S113, YES), the signal processing unit 110 ends the performance of the series of processing illustrated in FIG. 5.

An example of the flow of a series of processing of the medical observation system according to the present embodiment has been described with reference to FIG. 5 particularly focusing on the processing of the signal processing unit.

<2.4. Example>

Next, an example of the medical observation system according to the present embodiment will be described. For example, FIG. 6 is an explanatory diagram for explaining an example of the medical observation system according to the present embodiment, and illustrates an example of a case where blood flow evaluation is performed before and after anastomosis of the intestine by fluorescence imaging using ICG as a fluorescent material.

Specifically, as illustrated in the upper diagram of FIG. 6, the first administration of a fluorescent agent is performed first before the anastomosis of the intestine, and the blood flow before the anastomosis is evaluated on the basis of a fluorescence image V200 corresponding to the detection result of fluorescence after the administration. For example, a reference numeral V201 schematically indicates a region in which the detection result (hereinafter, also referred to as "first fluorescent component" for convenience) of fluorescence emitted from ICG contained in the fluorescent agent administered for the first time is detected. That is, the blood circulation state (for example, how far the blood flow has reached) is checked by the region V201 corresponding to the first fluorescent component presented in the fluorescence image V200, and the anastomosis site is determined according to the result of the check.

Subsequently, the second administration of the fluorescent agent is performed after the anastomosis, and the blood flow after the anastomosis is evaluated on the basis of a fluorescence image corresponding to the detection result of fluorescence after the administration.

For example, a fluorescence image V210 illustrated in the lower left of FIG. 6 illustrates an example of an output image presented after the second administration of the fluorescent agent at the time of the operation in the normal observation mode. Specifically, a reference numeral V211 schematically indicates the anastomosis site. Further, a reference numeral V213 schematically indicates a region corresponding to the first fluorescent component. On the other hand, a reference numeral V215 schematically indicates a region in which the detection result (hereinafter, also referred to as "second fluorescent component" for convenience) of fluorescence emitted from ICG contained in the fluorescent agent administered for the second time is detected. That is, in the fluorescence image V210 presented in the normal observation mode, the first fluorescent component remains in the fluorescence image V210, and the fluorescence intensity is added in the corresponding area V213. In view of such characteristics, it is difficult to determine which part in the fluorescence image V210 corresponds to the second fluorescent component, and as a result, it may be difficult to compare the time of the first administration of the fluorescent agent (that is, before anastomosis) with the time of the second administration of the fluorescent agent (that is, after anastomosis).

On the other hand, a fluorescence image V220 illustrated in the lower right of FIG. 6 illustrates an example of an output image presented after the second administration of the fluorescent agent at the time of the operation in the difference display mode. Specifically, a reference numeral V221 schematically indicates the anastomosis site. Further, a reference numeral V223 schematically indicates a region corresponding to the second fluorescent component. That is, in the fluorescence image V220 presented in the difference display mode, since the influence of the first fluorescent component is suppressed, the region V223 corresponding to the second fluorescent component can be visually recognized with the same visibility as the fluorescence image V200 presented after the first administration of the fluorescent agent. From such characteristics, at the time of operation in the difference display mode, it is possible to easily compare the time of the first administration of the fluores- cent agent (that is, before anastomosis) with the time of the second administration of the fluorescent agent (that is, after anastomosis).

The example of the medical observation system according to the present embodiment has been described above with reference to FIG. 6.

<2.5. Modification>

Next, as a modification of the medical observation system according to the present embodiment, another example of the functional configuration of the medical observation system will be described.

First Modification

Figure 7:
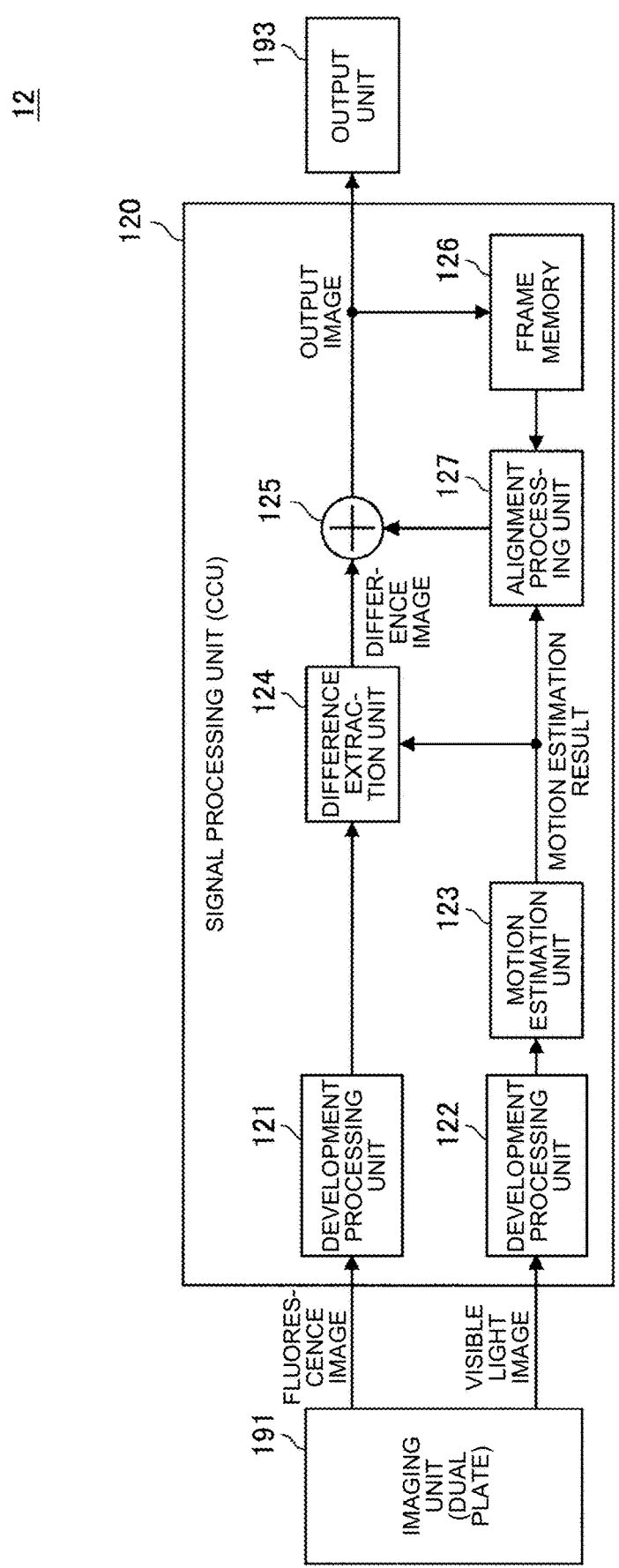
FIG. 7 is a block diagram illustrating an example of a functional configuration of a medical observation system according to a first modification.

First, an example of a configuration of a medical observation system according to a first modification will be described with reference to FIG. 7. FIG. 7 is a block diagram illustrating an example of a functional configuration of the medical observation system according to the first modification. Note that, in the following description, in a case where the medical observation system according to the present modification is particularly described, it is also referred to as "medical observation system 12" for convenience.

As illustrated in FIG. 7, the medical observation system 12 includes the imaging unit 191, a signal processing unit 120, and the output unit 193. Note that the output unit 193 is substantially similar to the output unit 193 in the example illustrated in FIGS. 1 and 2, and thus detailed description thereof is omitted.

The imaging unit 191 is configured as a so-called dual plate camera, separates incident light into visible light and fluorescence (for example, in the case of ICG, infrared light) emitted by a fluorescent material, and detects the respective rays by different image sensors, thereby individually outputting detection results of the respective rays. Note that the configuration for separating incident light into visible light and fluorescence is not particularly limited. As a specific example, incident light may be separated into visible light and fluorescence by using a color separation optical system configured using an optical film that separates incident light according to wavelength characteristics such as a dichroic film. On the basis of the above configuration, a fluorescence image and a visible light image are individually output from the imaging unit 191 to the signal processing unit 120.

The signal processing unit 120 includes development processing units 121 and 122, a motion estimation unit 123, a difference extraction unit 124, an addition unit 125, a frame memory 126, and an alignment processing unit 127. Note that the development processing unit 121, the difference extraction unit 124, the addition unit 125, the frame memory 126, and the alignment processing unit 127 are substantially similar to the development processing unit 111, the difference extraction unit 113, the addition unit 114, the frame memory 115, and the alignment processing unit 116 in the example illustrated in FIG. 2, and thus detailed description thereof is omitted.

The development processing unit 122 performs predetermined image processing (so-called development processing) on an image signal corresponding to the detection result of visible light output from the imaging unit 191 every predetermined unit period (for example, every frame) to generate a visible image. The development processing unit 122 then outputs the visible light image generated on the basis of the image processing to the motion estimation unit 123.

The motion estimation unit 123 estimates a relative motion (in other words, a motion of an affected part in the image) between the imaging unit 191 and a subject (for example, an affected part to be observed) on the basis of the visible light image output from the development processing unit 122. Note that the method by which the motion estimation unit 123 estimates the motion of the affected part in the image is similar to that of the motion estimation unit 112 in the example illustrated in FIG. 2 except that the type of image used for the estimation is different, and thus detailed description thereof is omitted. The motion estimation unit 123 then outputs the estimation result of the motion of the affected part in the image to the difference extraction unit 124 and the alignment processing unit 127.

As described above, in the medical observation system 12 according to the present modification, the output image (for example, the fluorescence image) is generated according to the imaging result of the affected part in which the light (for example, fluorescence) belonging to a first wavelength band corresponding to a drug (for example, a fluorescent agent) to be used is set as an imaging target. On the other hand, the motion of the affected part in the image is estimated according to the imaging result of the affected part in which light (for example, visible light) belonging to a second wavelength band different from the first wavelength band is set as the imaging target. In the visible light image, the subject (the affected part) tends to be recognized more clearly than in the fluorescence image. In view of such characteristics, by using the visible light image for estimating the motion of the affected part in the image, the accuracy of the estimation can be further improved as compared with the case of using the fluorescence image.

Note that the above is only an example, and does not necessarily limit the configuration of the medical observation system 12 according to the present modification. As a specific example, the configuration of the imaging unit 191 is not limited to the example of the so-called dual plate camera as long as it is possible to individually capture images in which rays belonging to different wavelength bands are imaging targets, such as the fluorescence image and the visible light image. As a specific example, the imaging unit 191 may be configured to capture the fluorescence image and the visible light image in a time division manner.

An example of the configuration of the medical observation system according to the first modification has been described with reference to FIG. 7.

Second Modification

Figure 8:
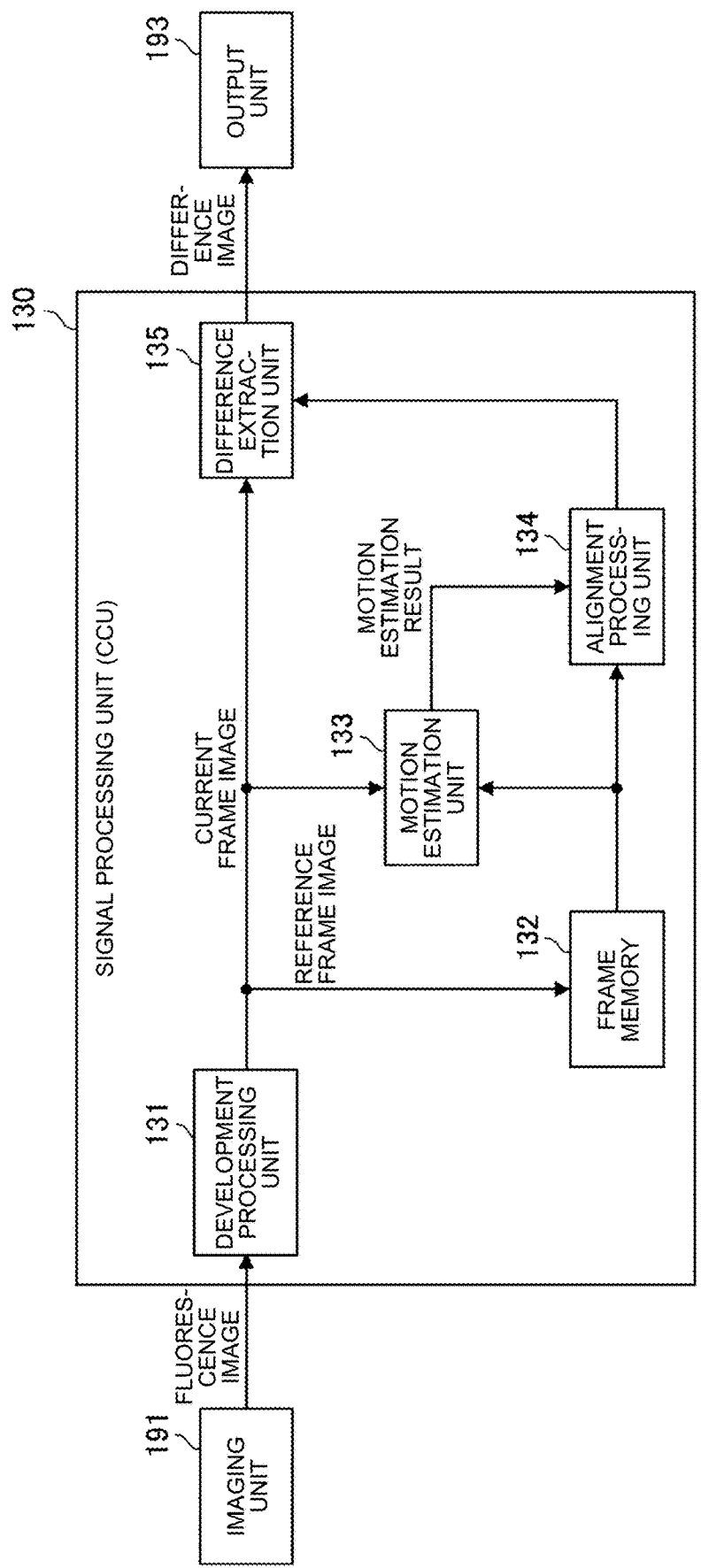
FIG. 8 is a block diagram illustrating an example of a functional configuration of a medical observation system according to a second modification.

Next, an example of a configuration of a medical observation system according to a second modification will be described with reference to FIG. 8. FIG. 8 is a block diagram illustrating an example of a functional configuration of the medical observation system according to the second modification. Note that, in the following description, in a case where the medical observation system according to the present modification is particularly described, it is also referred to as "medical observation system 13" for convenience.

As illustrated in FIG. 7, the medical observation system 12 includes the imaging unit 191, a signal processing unit 130, and the output unit 193. Note that the imaging unit 191 and the output unit 193 are substantially similar to the imaging unit 191 and the output unit 193 in the example illustrated in FIGS. 1 and 2, and thus detailed description thereof is omitted.

The signal processing unit 130 includes a development processing unit 131, a frame memory 132, a motion estimation unit 133, an alignment processing unit 134, and a difference extraction unit 135. Note that the development processing unit 131 is substantially similar to the development processing unit 111 in the example illustrated in FIGS. 1 and 2, and thus detailed description thereof is omitted.

The development processing unit 131 outputs an image (a fluorescence image) corresponding to the development result every predetermined unit period (for example, every frame) to the motion estimation unit 133 and the difference extraction unit 135. Note that, in the following description, for convenience, it is assumed that the development processing unit 131 outputs a fluorescence image for each frame.

Furthermore, in the medical observation system 13 according to the present modification, the fluorescence image output from the development processing unit 131 at the timing when a predetermined trigger is received is held in the frame memory 132. Note that, in the following description, the fluorescence image held in the frame memory 132 is also referred to as "reference frame image". Further, the fluorescence image sequentially output from the development processing unit 131 to the motion estimation unit 133 and the difference extraction unit 135 is also referred to as "current frame image". That is, the reference frame image corresponds to the fluorescence image output from the development processing unit 131 in the frame before the current frame image is output from the development processing unit 131. That is, in the present modification, the reference frame corresponds to an example of "first fluorescence image", and the current frame image corresponds to an example of "second fluorescence image".

The motion estimation unit 133 compares the current frame image output from the development processing unit 131 with the reference frame image held in the frame memory 132 to estimate a relative motion (in other words, a motion of an affected part in an image) between the imaging unit 191 and a subject (for example, an affected part to be observed). That is, the motion of the affected part in the image estimated at this time is based on the relationship in position and attitude between the imaging unit 191 and the subject, the relationship changing in the period between the timing when the reference frame image is captured and the timing when the current frame image is captured. The motion estimation unit 133 then outputs the estimation result of the motion of the affected part in the image to the alignment processing unit 134.

The alignment processing unit 134 reads the reference frame image held in the frame memory 132, and shifts the reference frame image on the basis of the estimation result of the motion of the affected part in the image output from the motion estimation unit 133. The alignment processing unit 134 then outputs the shifted reference frame image to the difference extraction unit 135. As a result, the alignment is performed between the current frame image and the reference frame image.

The difference extraction unit 135 calculates (extracts) a difference between the current frame image output from the development processing unit 131 and the reference frame image after the alignment output from the alignment processing unit 134, and generates a difference image corresponding to the calculation result of the difference. The difference extraction unit 135 then causes the output unit 193 to output the difference image generated.

The difference image presented as described above is an image in which the influence of a fluorescent component captured as the reference frame image, which becomes apparent in the current frame image, is suppressed. Using such characteristics, for example, under a situation in which the administration of the fluorescent agent and the fluorescence imaging are repeatedly performed, control may be executed such that the reference frame image is held at the timing of the second and subsequent administrations of the fluorescent agent. With such control, it is also possible to output a fluorescence image (for example, the fluorescence image V111 illustrated in FIG. 4) in which the influence of fluorescence emitted by the fluorescent material contained in the previously administered fluorescent agent is suppressed via the output unit 193.

Note that the above is only an example, and does not necessarily limit the configuration of the medical observation system 12 according to the present modification. As a specific example, it is also possible to combine the medical observation system 13 according to the present modification with the medical observation system 12 according to second modification described above. That is, in the medical observation system 13 according to the present modification, the visible light image may be used for estimating the motion of the affected part in the image. In this case, it suffices that, with respect to the visible light image, the reference frame image is held in the frame memory 132 separately from the fluorescence image, and the motion of the affected part in the image is estimated on the basis of the comparison between the current frame image (the visible light image) and the reference frame image.

An example of the configuration of the medical observation system according to the second modification has been described with reference to FIG. 8.

3. EXAMPLE OF HARDWARE CONFIGURATION

Figure 9:
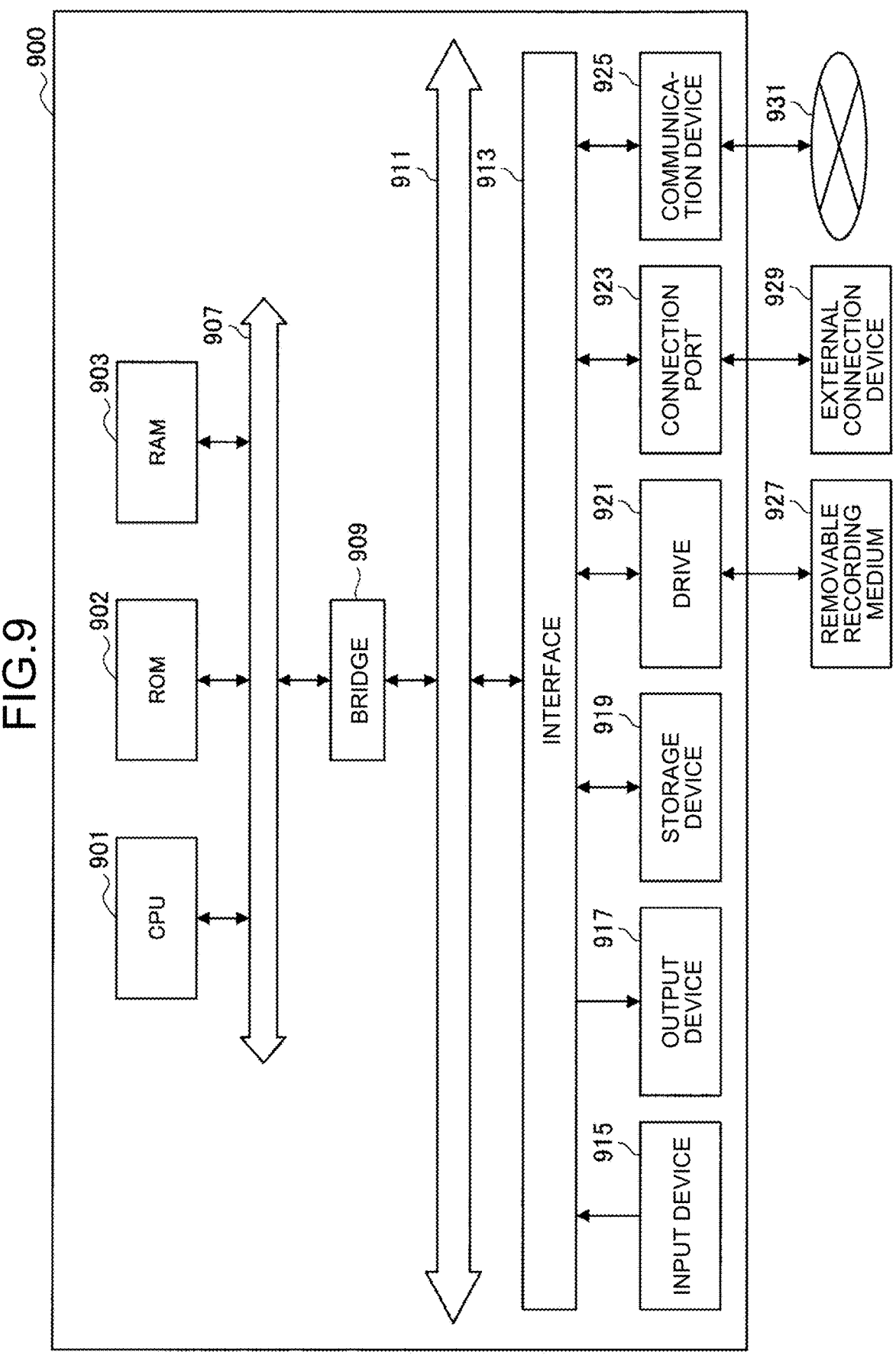
FIG. 9 is a functional block diagram illustrating a configuration example of a hardware configuration of an information processing apparatus constituting the medical observation system according to the embodiment.

Next, an example of a hardware configuration of an information processing apparatus (for example, the signal processing unit 110 illustrated in FIGS. 1 and 2 or the like) that performs various types of processing in the medical observation system according to the present embodiment will be described in detail with reference to FIG. 9. FIG. 9 is a functional block diagram illustrating a configuration example of a hardware configuration of an information processing apparatus constituting the medical observation system according to one embodiment of the present disclosure.

An information processing apparatus 900 constituting the medical observation system according to the present embodiment mainly includes a CPU 901, a ROM 902, and a RAM 903. In addition, the information processing apparatus 900 further includes a host bus 907, a bridge 909, an external bus 911, an interface 913, an input device 915, an output device 917, a storage device 919, a drive 921, a connection port 923, and a communication device 925.

The CPU 901 functions as an arithmetic processing unit and a control device, and controls all or part of the operation in the information processing apparatus 900 according to various types of programs recorded in the ROM 902, the RAM 903, the storage device 919, or a removable recording medium 927. The ROM 902 stores programs, arithmetic parameters, and the like used by the CPU 901. The RAM 903 primarily stores programs used by the CPU 901, parameters that appropriately change in the execution of the programs, and the like. These units are mutually connected by the host bus 907 including an internal bus such as a CPU bus. Note that each configuration of the signal processing unit 110 illustrated in FIGS. 1 and 2, that is, the development processing unit 111, the motion estimation unit 112, the difference extraction unit 113, the addition unit 114, and the alignment processing unit 116 can be implemented by the CPU 901.

The host bus 907 is connected to the external bus 911 such as a peripheral component interconnect/interface (PCI) bus via the bridge 909. In addition, the input device 915, the output device 917, the storage device 919, the drive 921, the connection port 923, and the communication device 925 are connected to the external bus 911 via the interface 913.

The input device 915 is an operation unit operated by a user, such as a mouse, a keyboard, a touch panel, a button, a switch, a lever, and a pedal. Furthermore, the input device 915 may be, for example, a remote control unit (so-called remote controller) using infrared rays or other radio waves, or an external connection device 929 such as a mobile phone or a PDA compatible with the operation of the information processing apparatus 900. Further, the input device 915 includes, for example, an input control circuit that generates an input signal on the basis of information input by the user using the operation unit described above and outputs the input signal to the CPU 901. By operating the input device 915, the user of the information processing apparatus 900 can input various types of data to the information processing apparatus 900 and instruct the information processing apparatus 900 on processing operations.

The output device 917 includes a device capable of visually or aurally notifying the user of information acquired. Examples of such a device include a display device such as a CRT display device, a liquid crystal display device, a plasma display device, an EL display device, and a lamp, an audio output device such as a speaker and a headphone, and a printer device. The output device 917 outputs, for example, results obtained by various types of processing performed by the information processing apparatus 900. Specifically, the display device displays results obtained by various types of processing performed by the information processing apparatus 900 as text or images. On the other hand, the audio output device converts an audio signal including reproduced audio data, acoustic data, or the like into an analog signal and outputs the analog signal. Note that the output unit 193 illustrated in FIGS. 1 and 2 can be implemented by the output device 917.

The storage device 919 is a data storage device configured as an example of a storage unit of the information processing apparatus 900. The storage device 919 includes, for example, a magnetic storage unit device such as a hard disk drive (HDD), a semiconductor storage device, an optical storage device, a magneto-optical storage device, or the like. The storage device 919 stores programs executed by the CPU 901, various types of data, and the like. Note that the frame memory 115 illustrated in FIGS. 1 and 2 can be implemented by any one of the storage device 919 and the RAM 903, or a combination thereof.

The drive 921 is a reader and writer for a recording medium, and is built in or externally attached to the information processing apparatus 900. The drive 921 reads information recorded in the removable recording medium 927 attached to the drive 921, such as a magnetic disk, an optical disk, a magneto-optical disk, or a semiconductor memory, and outputs the information to the RAM 903. Moreover, the drive 921 can also write a record in the removable recording medium 927 attached to the drive 921, such as a magnetic disk, an optical disk, a magneto-optical disk, or a semiconductor memory. The removable recording medium 927 is, for example, a DVD medium, an HD-DVD medium, a Blu-ray (registered trademark) medium, or the like. Furthermore, the removable recording medium 927 may be a CompactFlash (CF) (registered trademark), a flash memory, a secure digital (SD) memory card, or the like. Further, the removable recording medium 927 may be, for example, an integrated circuit (IC) card on which a non-contact IC chip is mounted, an electronic device, or the like.

The connection port 923 is a port for directly connecting to the information processing apparatus 900. Examples of the connection port 923 include a universal serial bus (USB) port, an IEEE 1394 port, a small computer system interface (SCSI) port, and the like. Other examples of the connection port 923 include an RS-232C port, an optical audio terminal, a high-definition multimedia interface (HDMI) (registered trademark) port, and the like. By connecting the external connection device 929 to the connection port 923, the information processing apparatus 900 directly acquires various types of data from the external connection device 929 or provides various types of data to the external connection device 929.

The communication device 925 is, for example, a communication interface including a communication device for connecting to a communication network (network) 931 or the like. The communication device 925 is, for example, a communication card for wired or wireless local area network (LAN), Bluetooth (registered trademark), or wireless USB (WUSB), or the like. Furthermore, the communication device 925 may be a router for optical communication, a router for asymmetric digital subscriber line (ADSL), a modem for various types of communications, or the like. For example, the communication device 925 can transmit and receive signals and the like to and from the Internet and other communication devices according to a predetermined protocol such as TCP/IP. Moreover, the communication network 931 connected to the communication device 925 includes a network connected in a wired or wireless manner or the like, and may be, for example, the Internet, a home LAN, infrared communication, radio wave communication, satellite communication, or the like.

An example of the hardware configuration that can implement the functions of the information processing apparatus 900 constituting the medical observation system according to the embodiment of the present disclosure has been described above. Each of the components described above may be configured using a general-purpose member, or may be configured by hardware specialized for the function of each component. Consequently, it is possible to appropriately change the hardware configuration to be used according to the technical level at the time of carrying out the present embodiment. Note that, although not illustrated in FIG. 9, it is needless to mention that various types of configurations corresponding to the information processing apparatus 900 constituting the medical observation system are included.

Note that a computer program for implementing each function of the information processing apparatus 900 constituting the medical observation system according to the present embodiment described above can be produced and mounted on a personal computer or the like. Furthermore, a computer-readable recording medium storing such a computer program can also be provided. The recording medium is, for example, a magnetic disk, an optical disk, a magneto-optical disk, a flash memory, or the like. Furthermore, the computer program described above may be distributed via, for example, a network without using a recording medium. Moreover, the number of computers that execute the computer program is not particularly limited. For example, a plurality of computers (for example, a plurality of servers and the like) may execute the computer program in cooperation with each other.

4. APPLICATION EXAMPLE

Next, an application example of the medical observation system according to one embodiment of the present disclosure will be described.

<4.1. First Application Example: Microscope Imaging System>

First, as a first application example, an example in a case where the medical observation system according to one embodiment of the present disclosure is configured as a microscope imaging system including a microscope unit will be described with reference to FIG. 10.

Figure 10:
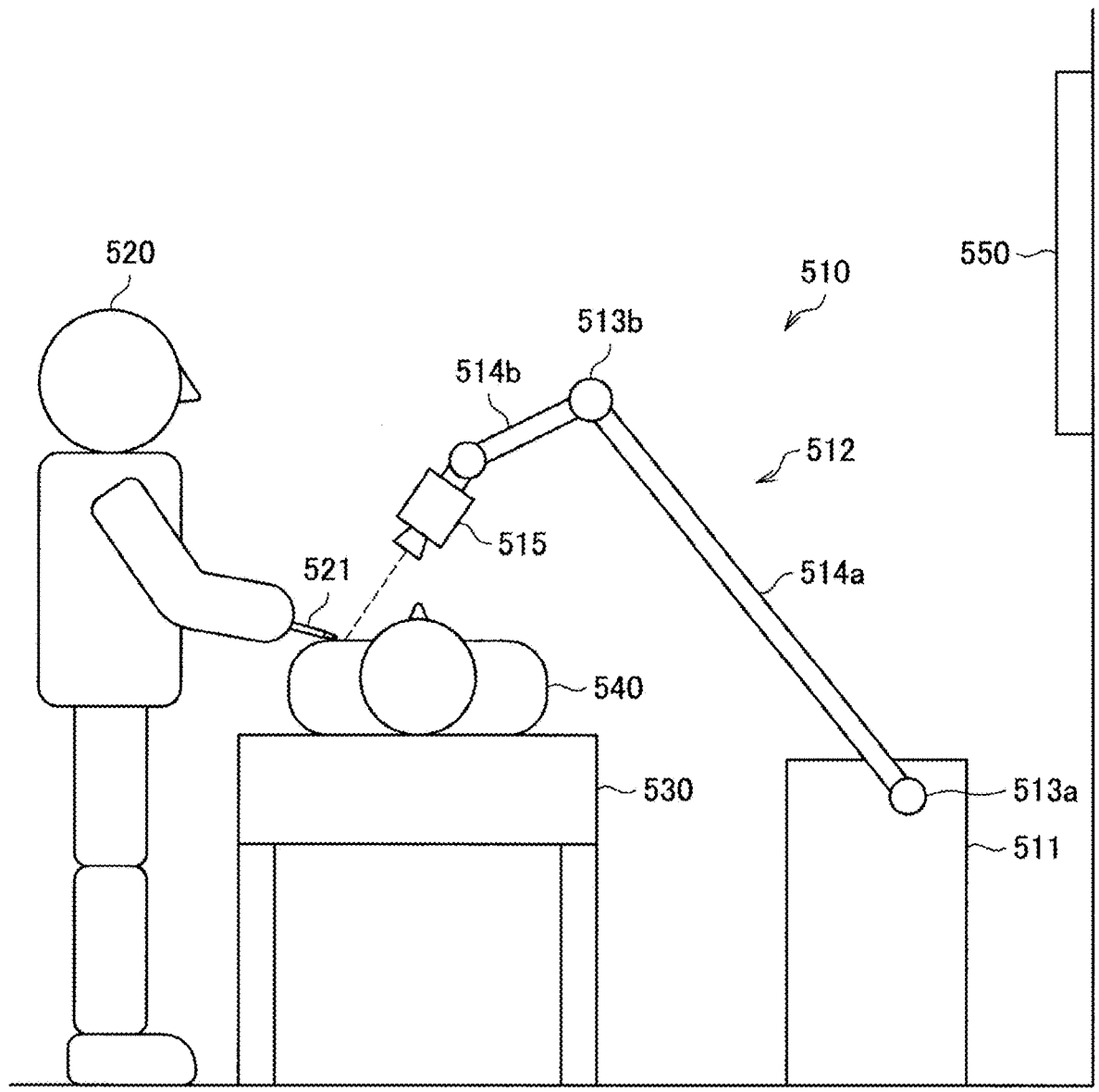
FIG. 10 is an explanatory diagram for explaining an application example of the medical observation system according to the embodiment.

FIG. 10 is an explanatory diagram for explaining an application example of the medical observation system according to one embodiment of the present disclosure, and illustrates an example of a schematic configuration of a microscope imaging system. Specifically, FIG. 10 illustrates an example of a case where a surgical video microscope device including an arm is used as an application example of a case where the microscope imaging system according to one embodiment of the present disclosure is used.

For example, FIG. 10 schematically illustrates a state of an operation using the surgical video microscope device. Specifically, referring to FIG. 10, a state where a doctor who is a practitioner (a user) 520 is performing surgery on an operation target (a patient) 540 on an operation table 830 using a surgical instrument 521 such as a scalpel, tweezers, or forceps is illustrated. Note that, in the following description, the operation is a generic term for various types of medical treatment performed by the doctor who is the user 520 on the patient who is the operation target 540, such as surgery and examination. Furthermore, in the example illustrated in FIG. 10, a state of surgery is illustrated as an example of the operation, but the operation using a surgical video microscope device 510 is not limited to surgery, and may be other various types of operations.

The surgical video microscope device 510 is provided beside the operation table 830. The surgical video microscope device 510 includes a base part 511 that is is a base, an arm part 512 extending from the base part 511, and an imaging unit 515 connected to a distal end of the arm part 512 as a distal end unit. The arm part 512 includes a plurality of joint parts 513a, 513b, and 513c, a plurality of links 514a and 514b connected by the joint parts 513a and 513b, and the imaging unit 515 provided at the distal end of the arm part 512. In the example illustrated in FIG. 10, the arm part 512 includes three joint parts 513a to 513c and two links 514a and 514b for the sake of simplicity, but in practice, the number and shape of the joint parts 513a to 513c and the links 514a and 514b, the directions of the drive shafts of the joint parts 513a to 513c, and the like may be appropriately set so as to achieve a desired degree of freedom in consideration of the degree of freedom of the position and attitude of the arm part 512 and the imaging unit 515.

The joint parts 513a to 513c have a function of rotatably connecting the links 514a and 514b to each other, and the drive of the arm part 512 is controlled by driving the rotation of the joint parts 513a to 513c. Here, in the following description, the position of each component of the surgical video microscope device 510 means a position (coordinates) in a space defined for drive control, and the attitude of each component means a direction (an angle) with respect to any axis in the space defined for drive control. Furthermore, in the following description, the drive (or the drive control) of the arm part 512 means that the position and attitude of each component member of the arm part 512 are changed (change is controlled) by driving (or drive control of) the joint parts 513a to 513c and driving (or drive control of) the joint parts 513a to 513c.

The imaging unit 515 is connected to the distal end of the arm part 512 as a distal end unit. The imaging unit 515 is a unit that acquires an image of an imaging target, and is, for example, a camera or the like capable of capturing a moving image or a still image. As illustrated in FIG. 10, attitudes and positions of the arm part 512 and the imaging unit 515 are controlled by the surgical video microscope device 510 such that the imaging unit 515 provided at the distal end of the arm part 512 captures a state of an operation site of the operation target 540. Note that the configuration of the imaging unit 515 connected to the distal end of the arm part 512 as a distal end unit is not particularly limited, and for example, the imaging unit 515 is configured as a microscope that acquires an enlarged image of the imaging target. Furthermore, the imaging unit 515 may be configured to be removable from the arm part 512. With such a configuration, for example, the imaging unit 515 based on the use application may be appropriately connected to the distal end of the arm part 512 as a distal end unit. Note that, as the imaging unit 515, for example, an imaging device to which the branching optical system according to the embodiment described above is applied can be applied. That is, in the present application example, the imaging unit 515 or the surgical video microscope device 510 including the imaging unit 515 can correspond to an example of "medical observation device". Further, the present description has been given focusing on the case where the imaging unit 515 is applied as a distal end unit, but the distal end unit connected to the distal end of the arm part 512 is not necessarily limited to the imaging unit 515.

Further, a display device 550 such as a monitor or a display is installed at a position facing the user 520. The image of the operation site captured by the imaging unit 515 is displayed as an electronic image on the display screen of the display device 550. The user 520 performs various treatments while viewing the electronic image of the operation site displayed on the display screen of the display device 550.

With the above configuration, it is possible to perform surgery while imaging the operation site by the surgical video microscope device 510.

Note that the present disclosure is not limited to the above, and the technology described above according to the present disclosure can be applied within a range not departing from the basic idea of the medical observation system according to one embodiment of the present disclosure. As a specific example, the technology described above according to the present disclosure can be appropriately applied not only to a system to which the endoscope or the operation microscope described above is applied, but also to a system in which an image of an affected part is captured by an imaging device of a desired form to enable observation of the affected part.

An example in a case where the medical observation system according to one embodiment of the present disclosure is configured as a microscope imaging system including a microscope unit has been described as the first application example with reference to FIG. 10.

<4.2. Second Application Example: Endoscopic Surgical System>

Next, as a second application example, an example in a case where the medical observation system according to one embodiment of the present disclosure is configured as an endoscopic surgical system including an endoscope unit will be described with reference to FIGS. 11 and 12.

Figure 11:
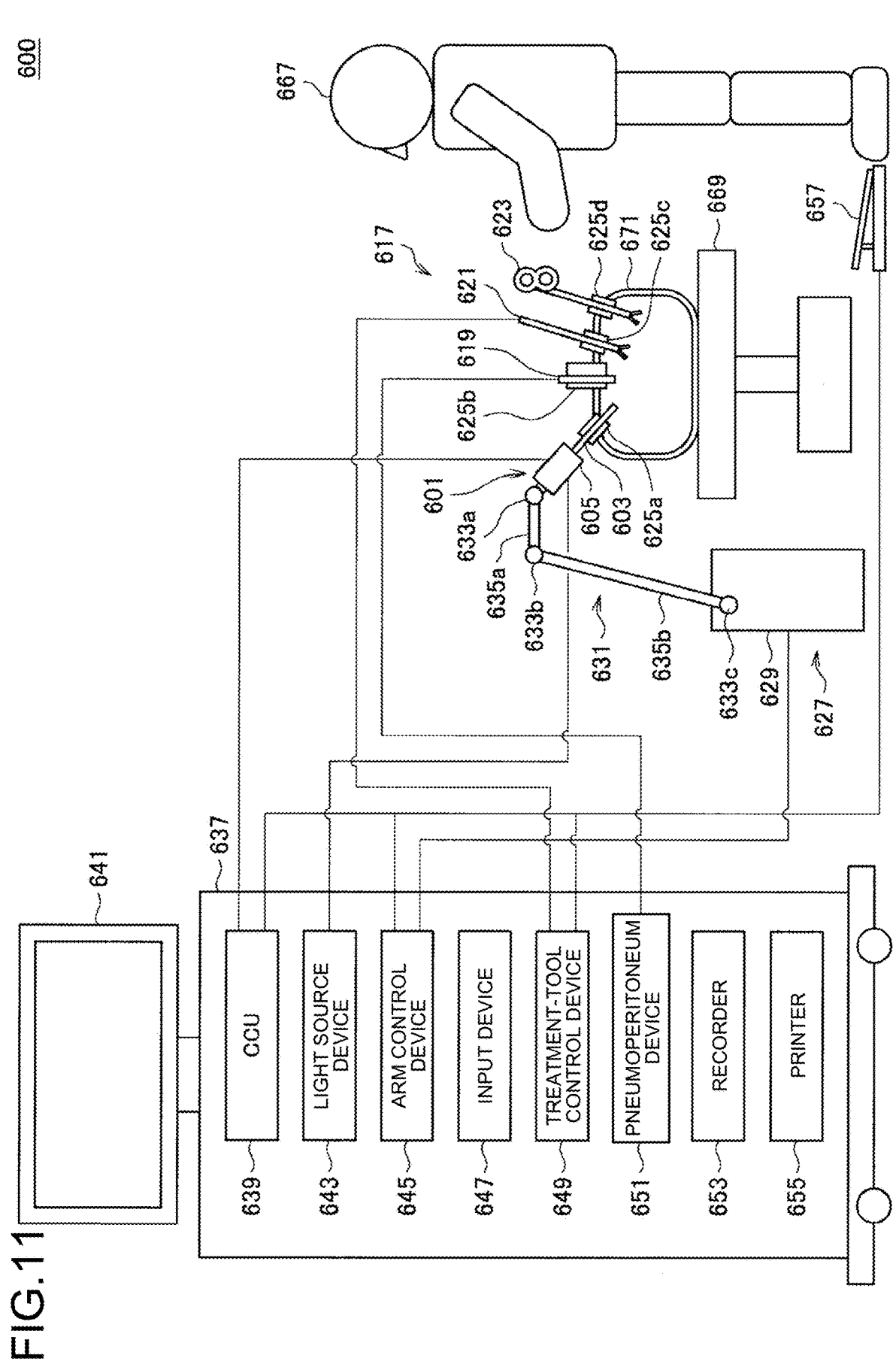
FIG. 11 is an explanatory diagram for explaining another application example of the medical observation system according to the embodiment.
Figure 12:
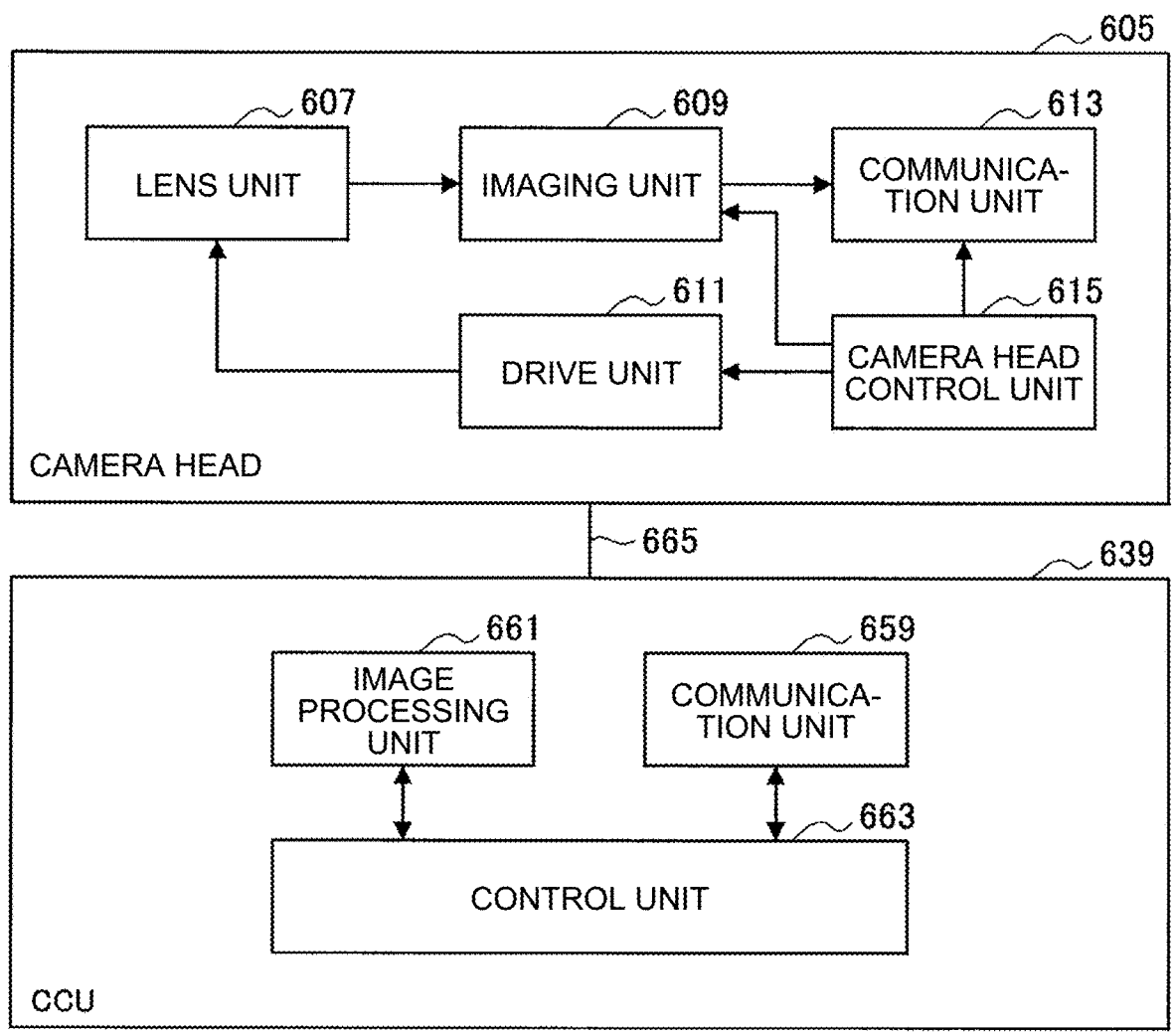
FIG. 12 is an explanatory diagram for explaining yet another application example of the medical observation system according to the embodiment.

FIGS. 11 and 12 are explanatory diagrams for explaining another application example of the medical observation system according to one embodiment of the present disclosure, and illustrate an example of a schematic configuration of an endoscopic surgical system.

For example, FIG. 11 is a diagram illustrating an example of a schematic configuration of an endoscopic surgical system to which the technology according to the present disclosure can be applied. FIG. 11 illustrates a state where an operator (a doctor) 667 is performing surgery on a patient 671 on a patient bed 669 using an endoscopic surgical system 600. As illustrated, the endoscopic surgical system 600 includes an endoscope 601, other surgical tools 617, a support arm device 627 that supports the endoscope 601, and a cart 637 on which various devices for endoscopic surgery are mounted.

In endoscopic surgery, instead of cutting and opening the abdominal wall, a plurality of cylindrical puncture instruments called trocars 625a to 625d are punctured into the abdominal wall. Then, a lens barrel 603 of the endoscope 601 and the other surgical tools 617 are inserted into the body cavity of the patient 671 from the trocars 625a to 625d. In the example illustrated, as the other surgical tools 617, a pneumoperitoneum tube 619, an energy treatment tool 621, and forceps 623 are inserted into the body cavity of the patient 671. Furthermore, the energy treatment tool 621 is a treatment tool that performs incision and detachment of tissue, sealing of a blood vessel, or the like by high-frequency current or ultrasonic vibration. However, the surgical tools 617 illustrated are only an example, and various types of surgical tools generally used in endoscopic surgery, such as tweezers and a retractor, may be used as the surgical tools 617.

An image of an operation site in the body cavity of the patient 671 captured by the endoscope 601 is displayed on a display device 641. While viewing the image of the operation site displayed on the display device 641 in real time, the operator 667 performs treatment such as resection of an affected part using the energy treatment tool 621 and the forceps 623. Note that, although not illustrated, the pneumoperitoneum tube 619, the energy treatment tool 621, and the forceps 623 are supported by the operator 667, an assistant, or the like during surgery.

(Support Arm Device)

The support arm device 627 includes an arm part 631 extending from a base part 629. In the example illustrated, the arm part 631 includes joint parts 633a, 633b, and 633c and links 635a and 635b, and is driven under the control of an arm control device 645. The endoscope 601 is supported by the arm part 631, and its position and attitude are controlled. As a result, stable fixation of the position of the endoscope 601 can be achieved.

(Endoscope)

The endoscope 601 includes the lens barrel 603 whose region with a predetermined length from the distal end is inserted into the body cavity of the patient 671, and a camera head 605 connected to the proximal end of the lens barrel 603. The example illustrates the endoscope 601 configured as a so-called rigid scope including the lens barrel 603 that is rigid, but the endoscope 601 may be configured as a so-called flexible scope including the lens barrel 603 that is flexible. Note that the camera head 605 or the endoscope 601 including the camera head 605 corresponds to an example of "medical observation device".

An opening into which an objective lens is fitted is provided at the distal end of the lens barrel 603. A light source device 643 is connected to the endoscope 601, and light generated by the light source device 643 is guided to the distal end of the lens barrel by a light guide extending inside the lens barrel 603, and is emitted toward an observation target (in other words, an imaging target) in the body cavity of the patient 671 via the objective lens. Note that the endoscope 601 may be a forward-viewing endoscope, an oblique-viewing endoscope, or a side-viewing endoscope.

An optical system and an imaging element are provided inside the camera head 605, and reflected light (observation light) from the observation target is condensed on the imaging element by the optical system. The observation light is photoelectrically converted by the imaging element, and an electric signal corresponding to the observation light, that is, an image signal corresponding to an observation image is generated. The image signal is transmitted to a camera control unit (CCU) 639 as RAW data. Note that the camera head 605 has a function of adjusting a magnification and a focal length by appropriately driving the optical system.

Note that, for example, in order to support stereoscopic viewing (3D display) or the like, a plurality of imaging elements may be provided in the camera head 605. In this case, a plurality of relay optical systems are provided inside the lens barrel 603 in order to guide the observation light to each of the plurality of imaging elements.

(Various Types of Devices Mounted on Cart)

The CCU 639 includes a central processing unit (CPU), a graphics processing unit (GPU), and the like, and integrally controls the operation of the endoscope 601 and the display device 641. Specifically, the CCU 639 performs, on the image signal received from the camera head 605, various types of image processing for displaying an image based on the image signal, such as development processing (demosaic processing). The CCU 639 provides the image signal subjected to the image processing to the display device 641. Furthermore, the CCU 639 transmits a control signal to the camera head 605 and controls the drive of the camera head 605. The control signal can include information related to imaging conditions such as a magnification and a focal length.

The display device 641 displays an image based on the image signal subjected to the image processing by the CCU 639 under the control of the CCU 639. In a case where the endoscope 601 supports high-resolution imaging such as 4K (the number of horizontal pixels 3840×the number of vertical pixels 2160) or 8K (the number of horizontal pixels 7680×the number of vertical pixels 4320), and/or in a case where the endoscope 601 supports 3D display, a display device capable of high-resolution display and/or a display device capable of 3D display can be used as the display device 641 corresponding to each case. In a case where the endoscope 601 supports high-resolution imaging such as 4K or 8K, a further immersive feeling can be obtained by using a display device with a size of 55 inches or more as the display device 641. Furthermore, a plurality of the display devices 641 with different resolutions and sizes may be provided depending on the application.

The light source device 643 includes, for example, a light source such as a light emitting diode (LED), and supplies irradiation light for capturing an operation site to the endoscope 601.

The arm control device 645 includes, for example, a processor such as a CPU, and operates according to a predetermined program to control the drive of the arm part 631 of the support arm device 627 according to a predetermined control system.

An input device 647 is an input interface for the endoscopic surgical system 600. The user can input various types of information and instructions to the endoscopic surgical system 600 via the input device 647. For example, the user inputs various types of information related to surgery, such as physical information of a patient and information related to the surgical method of the surgery, via the input device 647. Furthermore, for example, the user inputs an instruction to drive the arm part 631, an instruction to change imaging conditions (the type, magnification, focal length, and the like of irradiation light) of the endoscope 601, an instruction to drive the energy treatment tool 621, and the like via the input device 647.

The type of the input device 647 is not limited, and various known input devices may serve as the input device 647. As the input device 647, for example, a mouse, a keyboard, a touch panel, a switch, a foot switch 657 and/or a lever or the like can be applied. In a case where the touch panel is used as the input device 647, the touch panel may be provided on the display surface of the display device 641.

Alternatively, the input device 647 may be, for example, a sensor included in a device worn by the user, such as a glasses-type wearable device or a head mounted display (HMD). In this case, various types of inputs are performed according to the user's motion or line of sight detected by these sensors. Further, the input device 647 includes a camera capable of detecting a motion of the user, and various types of inputs are performed according to a gesture or a line of sight of the user detected from a video captured by the camera. Furthermore, the input device 647 includes a microphone capable of collecting a user's voice, and various types of inputs are performed by voice via the microphone. As described above, the input device 647 is configured to be able to input various types of information in a non-contact manner, and thus, in particular, the user (for example, the operator 667) belonging to a clean area can operate a device belonging to an unclean area in a non-contact manner. In addition, since the user can operate the device without releasing his/her hand from the holding surgical tool, the convenience of the user is improved.

A treatment-tool control device 649 controls the drive of the energy treatment tool 621 for cauterization and incision of tissues, sealing of a blood vessel, or the like. A pneumoperitoneum device 651 feeds gas into the body cavity of the patient 671 via the pneumoperitoneum tube 619 in order to inflate the body cavity of the patient 671 for the purpose of securing a field of view of the endoscope 601 and an operating space of the operator. A recorder 653 is a device capable of recording various types of information related to surgery. A printer 655 is a device capable of printing various types of information related to surgery in various formats such as text, image, or graph.

Hereinafter, a particularly characteristic configuration of the endoscopic surgical system 600 will be described in more detail.

(Support Arm Device)

The support arm device 627 includes the base part 629 that is a base and the arm part 631 extending from the base part 629. In the illustrated example, the arm part 631 includes a plurality of the joint parts 633*a*, 633*b*, and 633*c* and a plurality of the links 635*a* and 635*b* connected by the joint part 633*b*, but in FIG. 11, the configuration of the arm part 631 is illustrated in a simplified manner for the sake of simplicity. In practice, the shape, number, and arrangement of the joint parts 633a to 633c and the links 635a and 635b, the directions of the rotation axes of the joint parts 633a to 633c, and the like can be appropriately set so that the arm part 631 has a desired degree of freedom. For example, the arm part 631 can be suitably configured to have six degrees of freedom or more. As a result, since the endoscope 601 can be freely moved within the movable range of the arm part 631, the lens barrel 603 of the endoscope 601 can be inserted into the body cavity of the patient 671 from a desired direction.

An actuator is provided in each of the joint parts 633a to 633c, and the joint parts 633a to 633c are configured to be rotatable around a predetermined rotation axis by driving the actuators. The drive of the actuator is controlled by the arm control device 645, so that the rotation angle of each of the joint parts 633a to 633c is controlled and the drive of the arm part 631 is controlled accordingly. As a result, control of the position and attitude of the endoscope 601 can be achieved. At this time, the arm control device 645 can control the drive of the arm part 631 by various types of known control methods such as force control or position control.

For example, as the operator 667 appropriately performs an operation input via the input device 647 (including the foot switch 657), the drive of the arm part 631 may be appropriately controlled by the arm control device 645 in response to the operation input, and the position and attitude of the endoscope 601 may be controlled. With this control, the endoscope 601 at the distal end of the arm part 631 can be moved from an arbitrary position to an arbitrary position and then fixedly supported at the position after the movement. Note that the arm part 631 may be operated by a so-called master-slave method. In this case, the arm part 631 can be remotely operated by the user via the input device 647 installed at a place away from an operating room.

Furthermore, in a case where the force control is applied, the arm control device 645 may execute so-called power assist control of receiving an external force from the user and driving the actuator of each of the joint parts 633a to 633c so that the arm part 631 smoothly moves in response to the external force. As a result, when the user moves the arm part 631 while directly touching the arm part 631, the arm part 631 can be moved with a relatively light force. Consequently, it is possible to more intuitively move the endoscope 601 with a simpler operation, and the convenience of the user can be improved.

Here, in endoscopic surgery, the endoscope 601 is generally supported by a doctor called a scopist. On the other hand, by using the support arm device 627, it is possible to more reliably fix the position of the endoscope 601 without manual operation, so that it is possible to stably obtain an image of the operation site and smoothly perform the surgery.

Note that the arm control device 645 is not necessarily provided in the cart 637. Furthermore, the arm control device 645 is not necessarily a single device. For example, the arm control device 645 may be provided in each of the joint parts 633a to 633c of the arm part 631 in the support arm device 627, and the drive control of the arm part 631 may be achieved by a plurality of arm control devices 645 cooperating with each other.

(Light Source Device)

The light source device 643 supplies the endoscope 601 with irradiation light for capturing an operation site. The light source device 643 includes, for example, a white light source including an LED, a laser light source, or a combination thereof. At this time, in a case where the white light source is configured by a combination of RGB laser light sources, the output intensity and output timing of each color (each wavelength) can be controlled with high accuracy, so that the white balance of the captured image can be adjusted in the light source device 643. Furthermore, in this case, by irradiating an observation target with laser light from each of the RGB laser light sources in a time division manner and controlling the drive of the imaging element of the camera head 605 in synchronization with the irradiation timing, it is also possible to capture an image corresponding to each RGB in a time division manner. According to this method, a color image can be obtained without providing a color filter in the imaging element.

Further, the drive of the light source device 643 may be controlled so as to change the intensity of light to be output every predetermined time. By controlling the drive of the imaging element of the camera head 605 in synchronization with the timing of the change of the light intensity to acquire images in a time division manner and combining the images, it is possible to generate an image of a high dynamic range without so-called blocked up shadows and blown out highlights.

Furthermore, the light source device 643 may be configured to be able to supply light in a predetermined wavelength band suitable for special light observation. In the special light observation, for example, so-called narrow band imaging is performed in which a predetermined tissue such as a blood vessel in a mucosal surface layer is captured with high contrast by irradiating light in a narrower band than irradiation light (that is, white light) at the time of normal observation using wavelength dependency of light absorption in a body tissue. Alternatively, in the special light observation, fluorescence imaging that obtains an image by fluorescence generated by irradiation with excitation light may be performed. In the fluorescence imaging, for example, fluorescence from a body tissue can be observed by irradiating the body tissue with excitation light (autofluorescence imaging), or a fluorescent image can be obtained by locally injecting a reagent such as indocyanine green (ICG) into a body tissue and irradiating the body tissue with excitation light according to a fluorescence wavelength of the reagent. The light source device 643 can be configured to be able to supply narrow band light and/or excitation light suitable for such special light observation.

(Camera Head and CCU)

The functions of the camera head 605 and the CCU 639 of the endoscope 601 will be described in more detail with reference to FIG. 12. FIG. 12 is a block diagram illustrating an example of functional configurations of the camera head 605 and the CCU 639 illustrated in FIG. 11.

Referring to FIG. 12, the camera head 605 includes a lens unit 607, an imaging unit 609, a drive unit 611, a communication unit 613, and a camera head control unit 615 as functions thereof. Further, the CCU 639 includes a communication unit 659, an image processing unit 661, and a control unit 663 as functions thereof. The camera head 605 and the CCU 639 are connected to be bidirectionally communicable by a transmission cable 665.

First, the functional configuration of the camera head 605 will be described. The lens unit 607 is an optical system provided at a connection portion with the lens barrel 603. Observation light taken from the distal end of the lens barrel 603 is guided to the camera head 605 and enters the lens unit 607. The lens unit 607 is configured by combining a plurality of lenses including a zoom lens and a focus lens. The optical characteristics of the lens unit 607 are adjusted so as to condense the observation light on the light receiving surface of the imaging element in the imaging unit 609. Furthermore, the zoom lens and the focus lens are configured to be movable in position on the optical axis in order to adjust the magnification and focal point of a captured image.

The imaging unit 609 includes an imaging element and is disposed at a subsequent stage of the lens unit 607. The observation light having passed through the lens unit 607 is condensed on the light receiving surface of the imaging element, and an image signal corresponding to an observation image is generated by photoelectric conversion. The image signal generated by the imaging unit 609 is provided to the communication unit 613.

As the imaging element constituting the imaging unit 609, for example, a complementary metal oxide semiconductor (CMOS) image sensor or a charge coupled device (CCD) image sensor that is capable of color imaging and has a Bayer array, is used, but the imaging element may be an image sensor for single-plate monochrome imaging. A plurality of image sensors for monochrome imaging may be used. Note that, as the imaging element, for example, an imaging element that can support capturing of a high-resolution image of 4K or more may be used. By obtaining the image of the operation site with high resolution, the operator 667 can grasp the state of the operation site in more detail, and can progress the surgery more smoothly.

Furthermore, the imaging element constituting the imaging unit 609 may be configured to include a pair of imaging elements for acquiring image signals for the right eye and the left eye, the image signals being adapted for 3D display. By performing 3D display, the operator 667 can more accurately grasp the depth of the living tissue in the operation site. Note that, in a case where the imaging unit 609 is configured as a dual plate type, a plurality of the lens units 607 are provided corresponding to the respective imaging elements.

Moreover, the imaging unit 609 is not necessarily provided in the camera head 605. For example, the imaging unit 609 may be provided immediately after the objective lens inside the lens barrel 603.

The drive unit 611 includes an actuator, and moves the zoom lens and the focus lens in the lens unit 607 by a predetermined distance along the optical axis under the control of the camera head control unit 615. As a result, the magnification and focus of the image captured by the imaging unit 609 can be appropriately adjusted.

The communication unit 613 includes a communication device for transmitting and receiving various types of information to and from the CCU 639. The communication unit 613 transmits the image signal obtained from the imaging unit 609 as RAW data to the CCU 639 via the transmission cable 665. At this time, in order to display the captured image of the operation site with as little delay as possible, the image signal is preferably transmitted by optical communication. This is because, at the time of surgery, the operator 667 performs surgery while observing the state of an affected part with the captured image, and thus, for safer and more reliable surgery, it is required to display a moving image of the operation site in real time as much as possible. In a case where optical communication is performed, the communication unit 613 includes a photoelectric conversion module that converts an electric signal into an optical signal. The image signal is converted into an optical signal by the photoelectric conversion module and then transmitted to the CCU 639 via the transmission cable 665.

Furthermore, the communication unit 613 receives a control signal for controlling the drive of the camera head 605 from the CCU 639. The control signal includes, for example, information related to imaging conditions such as information for specifying a frame rate of a captured image, information for specifying imaging conditions (a shutter speed, an aperture, a gain, and the like) at the time of imaging, and/or information for specifying a magnification and a focus of a captured image. The communication unit 613 provides the received control signal to the camera head control unit 615. Note that the control signal from the CCU 639 may also be transmitted by optical communication. In this case, the communication unit 613 includes a photoelectric conversion module that converts an optical signal into an electric signal, and the control signal is converted into an electric signal by the photoelectric conversion module and then provided to the camera head control unit 615.

Note that the imaging conditions such as the frame rate, the exposure value, the magnification, and the focus described above are automatically set by the control unit 663 of the CCU 639 on the basis of the acquired image signal. That is, a so-called auto exposure (AE) function, an auto focus (AF) function, and an auto white balance (AWB) function are implemented by the CCU 639 and the endoscope 601.

The camera head control unit 615 controls the drive of the camera head 605 on the basis of the control signal from the CCU 639 received via the communication unit 613. For example, the camera head control unit 615 controls the drive of the imaging element in the imaging unit 609 on the basis of information to specify a frame rate of a captured image and/or information to specify a shutter speed or an aperture at the time of imaging. Furthermore, for example, the camera head control unit 615 appropriately moves the zoom lens and the focus lens of the lens unit 607 via the drive unit 611 on the basis of the information to specify the magnification and focal point of the captured image. The camera head control unit 615 may further have a function of storing information for identifying the lens barrel 603 and the camera head 605.

Note that by arranging the lens unit 607, the imaging unit 609, and the like in a sealed structure with high airtightness and waterproofness, the camera head 605 can have resistance to autoclave sterilization processing.

Next, the functional configuration of the CCU 639 will be described. The communication unit 659 includes a communication device for transmitting and receiving various types of information to and from the camera head 605. The communication unit 659 receives an image signal transmitted from the camera head 605 via the transmission cable 665. At this time, as described above, the image signal can be suitably transmitted by optical communication. In this case, the communication unit 659 includes a photoelectric conversion module that converts an optical signal into an electric signal. The communication unit 659 provides the image signal converted into the electric signal to the image processing unit 661.

Further, the communication unit 659 transmits a control signal for controlling the drive of the camera head 605 to the camera head 605. The control signal may also be transmitted by optical communication.

The image processing unit 661 performs various types of image processing on the image signal that is RAW data transmitted from the camera head 605. Examples of the image processing include various types of known signal processing such as development processing, high image quality processing (band emphasis processing, super-resolution processing, noise reduction (NR) processing, and/or camera shake correction processing), and/or enlargement processing (electronic zoom processing). In addition, the image processing unit 661 performs detection processing on the image signal for performing AE, AF, and AWB.

The image processing unit 661 includes a processor such as a CPU or a GPU, and the processor operates according to a predetermined program, so that the image processing and the detection processing described above can be performed. Note that, in a case where the image processing unit 661 includes a plurality of GPUs, the image processing unit 661 appropriately divides information related to an image signal, and performs image processing in parallel by the plurality of GPUs.

The control unit 663 executes various types of control related to imaging of an operation site by the endoscope 601 and display of the captured image. For example, the control unit 663 generates a control signal for controlling the drive of the camera head 605. At this time, in a case where the imaging conditions are input by a user, the control unit 663 generates a control signal on the basis of the input by the user. Alternatively, in a case where the AE function, the AF function, and the AWB function are mounted on the endoscope 601, the control unit 663 appropriately calculates optimum exposure conditions, a focal length, and a white balance on the basis of a result of the detection processing by the image processing unit 661, and generates a control signal.

Moreover, the control unit 663 causes the display device 641 to display the image of the operation site on the basis of the image signal subjected to the image processing by the image processing unit 661. At this time, the control unit 663 recognizes various types of objects in the operation site image using various types of image recognition technologies. For example, the control unit 663 can recognize a surgical tool such as forceps, a specific living body site, bleeding, mist at the time of using the energy treatment tool 621, and the like by detecting the shape of the edge, the color, and the like of the object included in the operation site image. When displaying the image of the operation site on the display device 641, the control unit 663 superimposes and displays various types of surgery support information on the image of the operation site using the recognition result. The surgery support information is superimposed and displayed, and presented to the operator 667, so that the surgery can be more safely and reliably advanced.

The transmission cable 665 connecting the camera head 605 and the CCU 639 is an electric signal cable compatible with electric signal communication, an optical fiber compatible with optical communication, or a composite cable thereof.

Here, wired communication is performed using the transmission cable 665 in the illustrated example, but communication between the camera head 605 and the CCU 639 may be performed wirelessly. In a case where the communication between the devices is performed wirelessly, it is not necessary to lay the transmission cable 665 in the operating room, so that a situation in which the movement of the medical staff in the operating room is hindered by the transmission cable 665 can be eliminated.

An example of the endoscopic surgical system 600 to which the technology according to the present disclosure can be applied has been described above. Note that, here, the endoscopic surgical system 600 has been described as an example, but the system to which the technology according to the present disclosure can be applied is not limited to such an example. For example, the technology according to the present disclosure may be applied to a flexible endoscope system for examination or a microscopic surgery system.

Note that the present disclosure is not limited to the above, and the technology described above according to the present disclosure can be applied within a range not departing from the basic idea of the medical observation system according to one embodiment of the present disclosure. As a specific example, the technology described above according to the present disclosure can be appropriately applied not only to a system to which the endoscope or the operation microscope described above is applied, but also to a system in which an image of an affected part is captured by an imaging device of a desired form to enable observation of the affected part.

In addition, it is needless to mention that a method of observing an affected part and a procedure to be applied are not particularly limited. For example, as an observation method (a treatment method) in which an aneurysm is an affected part to be observed, a method using a stent or a method using a flow diverter is known in addition to the clipping method described above. In addition, the treatment tool to be used may be different depending on the observation method and the procedure to be applied. Even in such a case, for example, in the case of the treatment tool held near the affected part, the technology according to the present disclosure is applied and the motion of the treatment tool is extracted from sequentially captured images of the affected part, so that the motion of the affected part can be detected.

As the second application example, an example in a case where the medical observation system according to one embodiment of the present disclosure is configured as the endoscopic surgical system including the endoscope unit has been described with reference to FIGS. 11 and 12.

5. CONCLUSION

As described above, in the medical image processing apparatus according to one embodiment of the present disclosure, the image processing unit acquires a first fluorescence image captured between the timing when the first drug is administered and the timing when the second drug is administered and a second fluorescence image captured after the timing when the second drug is administered. In addition, the image processing unit generates an output image in which fluorescence generated by the second drug is enhanced on the basis of the first fluorescence image and the second fluorescence image.

With the above configuration, under a situation in which the administration of a fluorescent agent and fluorescence imaging are repeatedly performed, it is possible to ensure visibility equivalent to that at the time of observation after the first administration of the fluorescent agent, even at the time of observation after the second and subsequent administrations of the fluorescent agent. That is, according to the medical observation system of one embodiment of the present disclosure, it is possible to observe an image acquired in response to a drug in a more suitable manner even in a situation in which the drug is administered a plurality of times.

Note that, a case where an image is generated on the basis of an imaging result of the imaging unit has been mainly described above, but the application target of the technology according to the present disclosure is not necessarily limited. As a specific example, the technology according to the present disclosure can also be applied to a system that performs signal processing on an optical signal such as fluorescence emitted from a fluorescent material or visible light. In this case, a part that acquires an optical signal corresponding to a detection result of light arriving from an observation target (for example, an affected part) in response to the administration of a drug (for example, a sensor that detects the light or a part that acquires a detection result from the sensor) corresponds to an example of "acquisition unit". In addition, the configuration corresponding to the signal processing unit (CCU) in the medical observation system according to the embodiment and the modification described above extracts the optical signal generated by a second drug on the basis of a first optical signal acquired between the timing when the first drug is administered and the timing when the second drug is administered and a second signal acquired after the timing when the second drug is administered. Note that the extraction of the optical signal generated by the second drug can be achieved on the basis of an idea similar to that of the method related to the generation of a fluorescence image in which the fluorescence generated by the second drug (for example, the fluorescent agent administered for the second and subsequent times) is enhanced in the medical observation system according to the embodiment and the modification described above. Furthermore, a configuration corresponding to the signal processing unit in this case corresponds to an example of "optical signal extraction unit". In addition, the above system corresponds to an example of "medical signal acquisition system".

Further, the above description has been given mainly focusing on fluorescence imaging performed using a fluorescent agent, but the application target of the technology according to the present disclosure is not necessarily limited. That is, the technology according to the present disclosure can be applied to an observation method in which a drug is administered to a patient and light in a wavelength band corresponding to the drug is observed. As a specific example, it is also possible to apply the technology according to the present disclosure to an observation method of administering a contrast medium other than a fluorescent agent to a patient and observing an image based on a detection result of light emitted by a material contained in the agent.

Although the preferred embodiments of the present disclosure have been described in detail with reference to the accompanying drawings, the technical scope of the present disclosure is not limited to such examples. It is obvious that a person having ordinary skill in the technical field of the present disclosure can conceive various types of changes or modifications within the scope of the technical idea described in the claims, and it is to be understood that these also belong to the technical scope of the present disclosure.

Furthermore, the effects described in the present specification are only illustrative or exemplary, and are not restrictive. That is, the technology according to the present disclosure can exhibit other effects obvious to those skilled in the art from the description of the present specification together with or instead of the above effects.

Note that the following configurations also belong to the technical scope of the present disclosure.

(1)

A medical image processing apparatus comprising
an image processing unit configured to
acquire a first fluorescence image captured between a timing when a first drug is administered and a first timing when a second drug is administered and a fluorescence intensity of a predetermined region starts to increase, and a second fluorescence image captured after the first timing and generate an output image in which fluorescence generated by the second drug is enhanced on a basis of the first fluorescence image and the second fluorescence image.

(2)

The medical image processing apparatus according to (1), wherein the second drug is the first drug.

(3)

The medical image processing apparatus according to (1) or (2), wherein a timing when each of the first drug and the second drug is administered is detected on a basis of a fluorescence image captured.

(4)

The medical image processing apparatus according to (3), wherein the image processing unit is configured to detect a minimum value of a change in luminance in time series in at least a part of an image after an administration of the second drug, and acquire a fluorescence image captured before a timing when the minimum value is detected as the first fluorescence image.

(5)

The medical image processing apparatus according to (1) or (2), wherein a timing when each of the first drug and the second drug is administered is detected on a basis of an input of a user.

(6)

The medical image processing apparatus according to any one of (1) to (5) further comprising a storage unit, wherein the image processing unit is configured to
extract a difference between frames of a captured image according to an imaging result of an affected part for each frame by an imaging unit as a difference image and accumulate the difference image in the storage unit,
output an output image corresponding to a result of accumulation of the difference image in the storage unit, and
output an output image in which fluorescence generated by the second drug is enhanced on the basis of the difference image accumulated after a timing when the second drug is administered by excluding the difference image accumulated in the storage unit before the timing from an output target as the output image.

(7)

The medical image processing apparatus according to (6), wherein the image processing unit is configured to
estimate a relative motion of the imaging unit and the affected part between frames on a basis of an imaging result of the affected part for each frame,
correct a shift between a first difference image corresponding to an extraction result of the difference and a second difference image accumulated in the storage unit on a basis of an estimation result of the motion, and
accumulate the first difference image corrected in the storage unit as the second difference image that is new.

(8)

The medical image processing apparatus according to (7), wherein the image processing unit is configured to
output the output image according to an imaging result of the affected part in which light belonging to a first wavelength band corresponding to at least one of the first drug and the second drug is set as an imaging target, and
estimate the motion according to an imaging result of the affected part in which light belonging to a second wavelength band different from the first wavelength band is set as an imaging target.

(9)

The medical image processing apparatus according to (8), wherein the light belonging to the second wavelength band includes light belonging to a visible light wavelength band.

(10)

The medical image processing apparatus according to any one of (1) to (5), further comprising
a storage unit, wherein
the image processing unit is configured to
hold the first fluorescence image in the storage unit,
extract a difference between the second fluorescence image and the first fluorescence image, and
output the output image corresponding to an extraction result of the difference.

(11)

The medical image processing apparatus according to any one of (1) (10), wherein the image processing unit is configured to output
a first output image based on the first fluorescence image and
a second output image in which fluorescence generated by the second drug is enhanced on a basis of the first fluorescence image and the second fluorescence image.

(12)

A method of driving a medical image processing apparatus comprising causing a computer to
acquire a first fluorescence image captured between a timing when a first drug is administered and a first timing when a second drug is administered and t of a predetermined region starts to increase, and a second fluorescence image captured after the first timing, and
generate an output image in which fluorescence generated by the second drug is enhanced on a basis of the first fluorescence image and the second fluorescence image.

(13)

A medical imaging system comprising:
a light source configured to emit excitation light of a fluorescent material contained in a drug to be administered to a patient;
an imaging unit configured to receive and capture an image of light including fluorescence generated by the drug; and
an image processing apparatus configured to generate an output image in which fluorescence generated by a second drug is enhanced on a basis of a first fluorescence image captured between a timing when a first drug is administered and a first timing when the second drug is administered and a fluorescence intensity of a predetermined region starts to increase, and a second fluorescence image captured after the first timing.

(14)

The medical imaging system according to (13) further comprising
an endoscope unit including a lens barrel to be inserted into a body cavity of the patient, wherein
the imaging unit captures an image corresponding to a result of condensation of light including the fluorescence by the endoscope unit.

(15)

The medical imaging system according to (13), further comprising
a microscope unit configured to acquire an enlarged image corresponding to a result of condensation of light including the fluorescence, wherein
the imaging unit captures the enlarged image acquired by the microscope unit.

(16)

A medical image processing apparatus comprising
an image processing unit configured to output an output image that corresponds to an imaging result of an affected part of a patient by an imaging unit and in which light belonging to a wavelength band corresponding to a drug to be administered to the patient is set as an imaging target, wherein
the image processing unit includes, as an operation mode,
a first mode for outputting an output image corresponding to an imaging result of the affected part at that time, and
a second mode for outputting an output image in which fluorescence generated by a second drug is enhanced on a basis of a first fluorescence image captured between a timing when a first drug is administered and a first timing when the second drug is administered and a fluorescence intensity of a predetermined region starts to increase, and a second fluorescence image captured after the first timing.

(17)

A medical signal acquisition system comprising:
a light source configured to emit light in a wavelength band corresponding to a drug to be administered to a patient;
an acquisition unit configured to acquire an optical signal belonging to a wavelength band corresponding to the drug; and
an optical signal extraction unit configured to extract an optical signal generated by a second drug on a basis of a first optical signal acquired between a timing when a first drug is administered and a first timing when the second drug is administered and a fluorescence intensity of a predetermined region starts to increase, and a second optical signal acquired after the first timing.

REFERENCE SIGNS LIST 11, 12, 13 MEDICAL OBSERVATION SYSTEM
110 SIGNAL PROCESSING UNIT
111 DEVELOPMENT PROCESSING UNIT
112 MOTION ESTIMATION UNIT
113 DIFFERENCE EXTRACTION UNIT
114 ADDITION UNIT
115 FRAME MEMORY
116, 127, 134 ALIGNMENT PROCESSING UNIT
120 SIGNAL PROCESSING UNIT
121 DEVELOPMENT PROCESSING UNIT
122 DEVELOPMENT PROCESSING UNIT
123, 133 MOTION ESTIMATION UNIT
124 DIFFERENCE EXTRACTION UNIT
125 ADDITION UNIT
126 FRAME MEMORY
130 SIGNAL PROCESSING UNIT
131 DEVELOPMENT PROCESSING UNIT
132 FRAME MEMORY
135 DIFFERENCE EXTRACTION UNIT
191 IMAGING UNIT

The invention claimed is:
1. A medical image processing apparatus comprising
an image processor configured to
acquire a first fluorescence image captured between a timing when a first drug is administered and a first timing when a second drug is administered and a fluorescence intensity of a predetermined region starts to increase, and a second fluorescence image captured after the first timing; and generate an output image in which fluorescence generated by the second drug is enhanced on a basis of the first fluorescence image and the second fluorescence image, wherein a timing when each of the first drug and the second drug is administered is detected on a basis of a fluorescence image captured, and the image processor is configured to detect a minimum value of a change in luminance in time series in at least a part of an image after an administration of the second drug, and acquire a fluorescence image captured before a timing when the minimum value is detected as the first fluorescence image.

2. The medical image processing apparatus according to claim 1, wherein the second drug is the first drug.

3. The medical image processing apparatus according to claim 1, wherein a timing when each of the first drug and the second drug is administered is detected on a basis of an input of a user.

4. The medical image processing apparatus according to claim 1, further comprising a memory, wherein the image processor is configured to extract a difference between frames of a captured image according to an imaging result of an affected part for each frame by an imager as a difference image and accumulate the difference image in the memory, output an output image corresponding to a result of accumulation of the difference image in the memory, and output an output image in which fluorescence generated by the second drug is enhanced on a basis of the difference image accumulated after the first timing by excluding the difference image accumulated in the memory before the first timing from an output target as the output image.

5. The medical image processing apparatus according to claim 4, wherein the image processor is configured to estimate a relative motion of the imager and the affected part between frames on a basis of an imaging result of the affected part for each frame, correct a shift between a first difference image corresponding to an extraction result of the difference and a second difference image accumulated in the memory on a basis of an estimation result of the relative motion, and accumulate the first difference image corrected in the memory as the second difference image that is new.

6. The medical image processing apparatus according to claim 5, wherein the image processor is configured to output the output image according to an imaging result of the affected part in which light belonging to a first wavelength band corresponding to at least one of the first drug and the second drug is set as an imaging target, and estimate the relative motion according to an imaging result of the affected part in which light belonging to a second wavelength band different from the first wavelength band is set as an imaging target.

7. The medical image processing apparatus according to claim 6, wherein the light belonging to the second wavelength band includes light belonging to a visible light wavelength band.

8. The medical image processing apparatus according to claim 1, further comprising a memory, wherein the image processor is configured to hold the first fluorescence image in the memory, extract a difference between the second fluorescence image and the first fluorescence image, and output the output image corresponding to an extraction result of the difference.

9. The medical image processing apparatus according to claim 1, wherein the image processor is configured to output a first output image based on the first fluorescence image and a second output image in which fluorescence generated by the second drug is enhanced on a basis of the first fluorescence image and the second fluorescence image.

10. A non-transitory computer readable storage device having computer readable instructions that, when executed by circuitry cause the circuitry to:

acquire a first fluorescence image captured between a timing when a first drug is administered and a first timing when a second drug is administered and a fluorescence intensity of a predetermined region starts to increase, and a second fluorescence image captured after the first timing, detect a minimum value of a change in luminance in time series in at least a part of an image after an administration of the second drug, acquire a fluorescence image captured before a timing when the minimum value is detected as the first fluorescence image, and generate an output image in which fluorescence generated by the second drug is enhanced on a basis of the first fluorescence image and the second fluorescence image.

11. A medical imaging system comprising:

a light source configured to emit excitation light of a fluorescent material contained in a drug to be administered to a patient;

an imager configured to receive and capture an image of light including fluorescence generated by the drug; and an image processor configured to generate an output image in which fluorescence generated by a second drug is enhanced on a basis of a first fluorescence image captured between a timing when a first drug is administered and a first timing when the second drug is administered and a fluorescence intensity of a predetermined region starts to increase, and a second fluorescence image captured after the first timing; and detect a minimum value of a change in luminance in time series in at least a part of an image after an administration of the second drug, and acquire a fluorescence image captured before a timing when the minimum value is detected as the first fluorescence image.

12. The medical imaging system according to claim 11, further comprising an endoscope including a lens barrel to be inserted into a body cavity of the patient, wherein the imager is configured to capture captures an image corresponding to a result of condensation of light including the fluorescence by the endoscope.

13. The medical imaging system according to claim 11, further comprising a microscope configured to acquire an enlarged image corresponding to a result of condensation of light including the fluorescence, wherein the imager is configured to capture the enlarged image acquired by the microscope.

14. The medical image processing apparatus according to claim 1, wherein:
the image processor is configured to output an output image that corresponds to an imaging result of an affected part of a patient by an imager and in which light belonging to a wavelength band corresponding to a drug to be administered to the patient is set as an imaging target, wherein
the image processor includes, as an operation mode,
a first mode for outputting an output image corresponding to an imaging result of the affected part at that time, and
a second mode for outputting an output image in which fluorescence generated by a second drug is enhanced on a basis of a first fluorescence image captured between a timing when a first drug is administered and a first timing when the second drug is administered and a fluorescence intensity of a predetermined region starts to increase, and a second fluorescence image captured after the first timing.

15. A medical signal acquisition system comprising:
a light source configured to emit light in a wavelength band corresponding to a drug to be administered to a patient;
an acquisition circuit configured to acquire an optical signal belonging to a wavelength band corresponding to the drug; and
an optical signal extraction circuit configured to
extract an optical signal generated by a second drug on a basis of a first optical signal acquired between a timing when a first drug is administered and a first timing when the second drug is administered and a fluorescence intensity of a predetermined region starts to increase, and a second optical signal acquired after the first timing, and
detect a minimum value of a change in luminance in time series in at least a part of an image after an administration of the second drug, and acquire an optical signal before a timing when the minimum value is detected as the first optical signal.

16. A medical image processing apparatus comprising:
a memory; and
an image processor configured to
acquire a first fluorescence image captured between a timing when a first drug is administered and a first timing when a second drug is administered and a fluorescence intensity of a predetermined region starts to increase, and a second fluorescence image captured after the first timing,
extract a difference between frames of a captured image according to an imaging result of an affected part for each frame by an imager as a difference image and accumulate the difference image in the memory,
output an output image corresponding to a result of accumulation of the difference image in the memory, and
output an output image in which fluorescence generated by the second drug is enhanced on a basis of the difference image accumulated after the first timing by excluding the difference image accumulated in the memory before the first timing from an output target as the output image.

17. The medical image processing apparatus according to claim 16, wherein the image processor is configured to
estimate a relative motion of the imager and the affected part between frames on a basis of an imaging result of the affected part for each frame,
correct a shift between a first difference image corresponding to an extraction result of the difference and a second difference image accumulated in the memory on a basis of an estimation result of the relative motion, and
accumulate the first difference image corrected in the memory as the second difference image that is new.

18. The medical image processing apparatus according to claim 17, wherein the image processor is configured to
output the output image according to an imaging result of the affected part in which light belonging to a first wavelength band corresponding to at least one of the first drug and the second drug is set as an imaging target, and
estimate the relative motion according to an imaging result of the affected part in which light belonging to a second wavelength band different from the first wavelength band is set as an imaging target.

19. The medical image processing apparatus according to claim 18, wherein the light belonging to the second wavelength band includes light belonging to a visible light wavelength band.

20. The medical image processing apparatus according to claim 16, wherein:
the image processor is configured to output an output image that corresponds to an imaging result of an affected part of a patient by an imager and in which light belonging to a wavelength band corresponding to a drug to be administered to the patient is set as an imaging target, wherein
the image processor includes, as an operation mode,
a first mode for outputting an output image corresponding to an imaging result of the affected part at that time, and
a second mode for outputting an output image in which fluorescence generated by a second drug is enhanced on a basis of a first fluorescence image captured between a timing when a first drug is administered and a first timing when the second drug is administered and a fluorescence intensity of a predetermined region starts to increase, and a second fluorescence image captured after the first timing.

\* \* \* \* \*